US012359026B2

(12) United States Patent
Hoare et al.

(10) Patent No.: US 12,359,026 B2
(45) Date of Patent: Jul. 15, 2025

(54) IN SITU GELLING ZWITTERIONIC HYDROGEL COMPOSITIONS, AND METHODS OF USE THEREOF

(71) Applicant: McMaster Unversity, Hamilton (CA)

(72) Inventors: Todd Hoare, Ancaster (CA); Jonathan Dorogin, Richmond Hill (CA); Zhicheng Pan, Hamilton (CA); Nahieli Iyeida Preciado Rivera, Hamilton (CA)

(73) Assignee: McMaster University, Hamilton (CA)

( * ) Notice: Subject to any disclaimer, the term of this patent is extended or adjusted under 35 U.S.C. 154(b) by 484 days.

(21) Appl. No.: 17/927,817

(22) PCT Filed: May 28, 2021

(86) PCT No.: PCT/CA2021/050731
§ 371 (c)(1),
(2) Date: Nov. 25, 2022

(87) PCT Pub. No.: WO2021/237369
PCT Pub. Date: Dec. 2, 2021

(65) Prior Publication Data

US 2023/0220166 A1 Jul. 13, 2023

Related U.S. Application Data

(60) Provisional application No. 63/031,169, filed on May 28, 2020.

(51) Int. Cl.
*C08J 3/075* (2006.01)
*A61L 27/26* (2006.01)
(Continued)

(52) U.S. Cl.
CPC ............... *C08J 3/075* (2013.01); *A61L 27/26* (2013.01); *A61L 27/52* (2013.01); *A61L 27/54* (2013.01);
(Continued)

(58) Field of Classification Search
CPC combination set(s) only.
See application file for complete search history.

(56) References Cited

U.S. PATENT DOCUMENTS

2017/0355799 A1* 12/2017 Veiseh ................. A61K 9/5036
2019/0321512 A1 10/2019 Hoare et al.

FOREIGN PATENT DOCUMENTS

WO WO-2017218507 A1 * 12/2017 ......... A61B 5/14532
WO WO2019087185 A1 5/2019

OTHER PUBLICATIONS

GhavamiNejad, A.; Park, C. H.; Kim, C. S., In situ synthesis of antimicrobial silver nanoparticles within antifouling zwitterionic hydrogels by catecholic redox chemistry for wound healing application. Biomacromolecules 2016, 17 (3), 1213-1223.

(Continued)

*Primary Examiner* — Peter A Salamon
(74) *Attorney, Agent, or Firm* — Smart & Biggar LP; Michael Fenwick

(57) ABSTRACT

The disclosure relates to an in situ-gelling hydrogel composition based on functionalized zwitterionic polymers. The resulting hydrogels exhibit highly anti-fouling, anti-adhesive, and lubricating properties to enable the fabrication of bulk hydrogels or hydrogel-based coatings of relevance to biomedical applications.

24 Claims, 18 Drawing Sheets

ZK (Ketone AAEM)
ZK (Ketone MDM)
ZK-co-A (Ketone-co-Aldehyde)
MDM + APS / 75°C Water HCl
AAEM + APS 75°C Water
DMEMAm + DiAAm + APS 75°C Water HCl
ZH (Hydrazide)
ZA (Aldehyde)
AA + APS / 75°C Water
ADH + EDC / pH 4.75
DMEMAm + APS / 75°C Water
HCl

(51) Int. Cl.
*A61L 27/52* (2006.01)
*A61L 27/54* (2006.01)
*C08J 3/24* (2006.01)
*C08L 33/26* (2006.01)

(52) U.S. Cl.
CPC .............. *C08J 3/246* (2013.01); *C08L 33/26* (2013.01); *A61L 2430/24* (2013.01); *C08J 2333/26* (2013.01)

(56) References Cited

OTHER PUBLICATIONS

Song, J.; Zhu, Y.; Zhang, J.; Yang, J.; Du, Y.; Zheng, W.; Wen, C.; Zhang, Y.; Zhang, L., Encapsulation of AgNPs within Zwitterionic Hydrogels for Highly Efficient and Antifouling Catalysis in Biological Environments. Langmuir 2018, 35 (5), 1563-1570.
Harbers, G. M.; Emoto, K.; Greef, C.; Metzger, S. W.; Woodward, H. N.; Mascali, J. J.; Grainger, D. W.; Lochhead, M. J., Functionalized Poly(ethylene glycol)-Based Bioassay Surface Chemistry That Facilitates Bio-Immobilization and Inhibits Nonspecific Protein, Bacterial, and Mammalian Cell Adhesion. Chemistry of Materials 2007, 19 (18), 4405-4414.
Monteiro, D. R.; Gorup, L. F.; Takamiya, A. S.; Ruvollo-Filho, A. C.; de Camargo, E. R.; Barbosa, D. B., The growing importance of materials that prevent microbial adhesion: antimicrobial effect of medical devices containing silver. International journal of antimicrobial agents 2009, 34 (2), 103-110.
Zhang, L.; Cao, Z.; Bai, T.; Carr, L.; Ella-Menye, J.-R.; Irvin, C.; Ratner, B. D.; Jiang, S., Zwitterionic hydrogels implanted in mice resist the foreign-body reaction. Nature Biotechnology 2013, 31, 553.
Jansen, L. E.; Amer, L. D.; Chen, E. Y. T.; Nguyen, T. V.; Saleh, L. S.; Emrick, T.; Liu, W. F.; Bryant, S. J.; Peyton, S. R., Zwitterionic PEG-PC hydrogels modulate the foreign body response in a modulus-dependent manner. Biomacromolecules 2018, 19 (7), 2880-2888.
Geagea, R.; Aubert, P. H.; Banet, P.; Sanson, N., Signal enhancement of electrochemical biosensors via direct electrochemical oxidation of silver nanoparticle labels coated with zwitterionic polymers. Chemical Communications 2015, 51 (2), 402-405.
Liu, N.; Xu, Z.; Morrin, A.; Luo, X., Low fouling strategies for electrochemical biosensors targeting disease biomarkers. Analytical Methods 2019, 11 (6), 702-711.
Zhao, W.; Zhu, Y.; Zhang, J.; Xu, T.; Li, Q.; Guo, H.; Zhang, J.; Lin, C.; Zhang, L., A comprehensive study and comparison of four types of zwitterionic hydrogels. Journal of Materials Science 2018, 53 (19), 13813-13825.
Laschewsky, A., Structures and Synthesis of Zwitterionic Polymers. Polymers 2014, 6 (5), 1544-1601.
Jiang, S.; Cao, Z., Ultralow-fouling, functionalizable, and hydrolyzable zwitterionic materials and their derivatives for biological applications. Advanced materials 2010, 22 (9), 920-932.
Bai, T.; Sun, F.; Zhang, L.; Sinclair, A.; Liu, S.; Ella-Menye, J. R.; Zheng, Y.; Jiang, S., Restraint of the differentiation of mesenchymal stem cells by a nonfouling zwitterionic hydrogel. Angewandte Chemie International Edition 2014, 53 (47), 12729-12734.
Yu, L.; Ding, J., Injectable hydrogels as unique biomedical materials. Chemical Society Reviews 2008, 37 (8), 1473-1481.
Smeets, N. M. B.; Bakaic, E.; Patenaude, M.; Hoare, T., Injectable poly (oligoethylene glycol methacrylate)-based hydrogels with tunable phase transition behaviours: Physicochemical and biological responses. Acta biomaterialia 2014, 10 (10), 4143-4155.
Chang, J.; Tao, Y.; Wang, B.; Guo, B.-h.; Xu, H.; Jiang, Y.-r.; Huang, Y., An in situ-forming zwitterionic hydrogel as vitreous substitute. Journal of Materials Chemistry B 2015, 3 (6), 1097-1105.
Li, Y.; Rodrigues, J.; Tomas, H., Injectable and biodegradable hydrogels: gelation, biodegradation and biomedical applications. Chemical Society Reviews 2012, 41 (6), 2193-2221.
Ren, Z.; Zhang, Y.; Li, Y.; Xu, B.; Liu, W., Hydrogen bonded and ionically crosslinked high strength hydrogels exhibiting Ca 2+-triggered shape memory properties and volume shrinkage for cell detachment. Journal of Materials Chemistry B 2015, 3 (30), 6347-6354.
Bakaic, E.; Smeets, N. M. B.; Badv, M.; Dodd, M.; Barrigar, O.; Siebers, E.; Lawlor, M.; Sheardown, H.; Hoare, T., Injectable and Degradable Poly (Oligoethylene glycol methacrylate) Hydrogels with Tunable Charge Densities as Adhesive Peptide-Free Cell Scaffolds. ACS Biomaterials Science & Engineering 2017, 4 (11), 3713-3725.
Smeets, N. M. B.; Bakaic, E.; Patenaude, M.; Hoare, T., Injectable and tunable poly (ethylene glycol) analogue hydrogels based on poly (oligoethylene glycol methacrylate). Chemical Communications 2014, 50 (25), 3306-3309.
Urosev, I.; Bakaic, E.; Alsop, R. J.; Rheinstadter, M. C.; Hoare, T., Tuning the properties of injectable poly (oligoethylene glycol methacrylate) hydrogels by controlling precursor polymer molecular weight. Journal of Materials Chemistry B 2016, 4 (40), 6541-6551.
Lutolf, M. P.; Lauer-Fields, J. L.; Schmoekel, H. G.; Metters, A. T.; Weber, F. E.; Fields, G. B.; Hubbell, J. A., Synthetic matrix metalloproteinase-sensitive hydrogels for the conduction of tissue regeneration: engineering cell-Invasion characteristics. Proceedings of the National Academy of Sciences 2003, 100 (9), 5413-5418.
Obara, K.; Ishihara, M.; Ishizuka, T.; Fujita, M.; Ozeki, Y.; Maehara, T.; Saito, Y.; Yura, H.; Matsui, T.; Hattori, H., Photocrosslinkable chitosan hydrogel containing fibroblast growth factor-2 stimulates wound healing in healing-impaired db/db mice. Biomaterials 2003, 24 (20), 3437-3444.
Qiu, Y.; Park, K., Environment-sensitive hydrogels for drug delivery. Advanced drug delivery reviews 2001, 53 (3), 321-339.
Blackman, L. D.; Gunatillake, P. A.; Cass, P.; Locock, K. E. S., An introduction to zwitterionic polymer behavior and applications in solution and at surfaces. Chem Soc Rev 2019, 48 (3), 757-770.
Lee, C.-J.; Wu, H.; Hu, Y.; Young, M.; Wang, H.; Lynch, D.; Xu, F.; Cong, H.; Cheng, G., Ionic Conductivity of Polyelectrolyte Hydrogels. ACS Applied Materials & Interfaces 2018, 10 (6), 5845-5852.
De France, K. J.; Chan, K. J. W.; Cranston, E. D.; Hoare, T., Enhanced mechanical properties in cellulose hanocrystal-poly (oligoethylene glycol methacrylate) injectable nanocomposite hydrogels through control of physical and chemical cross-linking. Biomacromolecules 2016, 17 (2), 649-660.
Pong, D.; Li, J.; Cui, M.; Wang, J.; Zhou, Y.; Luo, L.; Wei, Y.; Ye, L.; Sun, H.; Yao, F., In Situ "Clickable" Zwitterionic Starch-Based Hydrogel for 3D Cell Encapsulation. ACS Appl Mater Interfaces 2016, 8 (7), 4442-55.
Sinclair, A.; O'Kelly, M. B.; Bai, T.; Hung, H. C.; Jain, P.; Jiang, S., Self-Healing Zwitterionic Microgels as a Versatile Platform for Malleable Cell Constructs and Injectable Therapies. Adv Mater 2018, 30 (39), e1803087.
Sundaram, H. S.; Han, X.; Nowinski, A. K.; Ella-Menye, J. R.; Wimbish, C.; Marek, P.; Senecal, K.; Jiang, S., One-step dip coating of zwitterionic sulfobetaine polymers on hydrophobic and hydrophilic surfaces. ACS Appl Mater Interfaces 2014, 6 (9), 6664-71.
Sundaram, H. S.; Han, X.; Nowinski, A. K.; Brault, N. D.; Li, Y.; Ella-Menye, J. R.; Amoaka, K. A.; Cook, K. E.; Marek, P.; Senecal, K.; Jiang, S., Achieving One-step Surface Coating of Highly Hydrophilic Poly(Carboxybetaine Methacrylate) Polymers on Hydrophobic and Hydrophilic Surfaces. Adv Mater Interfaces 2014, 1 (6).
He, H.; Xiao, Z.; Zhou, Y.; Chen, A.; Xuan, X.; Li, Y.; Guo, X.; Zheng, J.; Xiao, J.; Wu, J., Zwitterionic poly (sulfobetaine methacrylate) hydrogels with optimal mechanical properties for improving wound healing in vivo. J Mater Chem B 2019, 7 (10), 1697-1707.
Chen, Y.; Wang, W.; Wu, D.; Nagao, M.; Hall, D. G.; Thundat, T.; Narain, R., Injectable Self-Healing Zwitterionic Hydrogels Based on Dynamic Benzoxaborole—Sugar Interactions with Tunable Mechanical Properties. Biomacromolecules 2018, 19 (2), 596-605.
Patenaude, M.; Campbell, S.; Kinio, D.; Hoare, T., Tuning Gelation Time and Morphology of Injectable Hydrogels Using Ketone-Hydrazide Cross-Linking. Biomacromolecules 2014, 15 (3), 781-790.

(56) References Cited

OTHER PUBLICATIONS

Lee, S. Y.; Lee, Y.; Le Thi, P.; Oh, D. H.; Park, K. D., Sulfobetaine methacrylate hydrogel-coated anti-fouling surfaces for implantable biomedical devices. Biomater Res 2018, 22, 3.
Lu, A.; Wu, Z.; Luo, X.; Li, S., Protein adsorption and macrophage uptake of zwitterionic sulfobetaine containing micelles. Colloids Surf B Biointerfaces 2018, 167, 252-259.
Su, Y.-I.; Li, C., Controlled adsorption of bovine serum albumin on poly(acrylonitrile)-based zwitterionic membranes. Reactive and Functional Polymers 2008, 68 (1), 161-168.
Du, H.; Chandaroy, P.; Hui, S. W., Grafted poly-(ethylene glycol) on lipid surfaces inhibits protein adsorption and cell adhesion. Biochim. Biophys_ Acta-Biomembr. 1997, 1326 (2), 236-248.
Xu, L. C.; Siedlecki, C. A., Protein adsorption, platelet adhesion, and bacterial adhesion to polyethylene-glycol-textured polyurethane biomaterial surfaces. J. Biomed. Mater. Res. Part B 2017, 105 (3), 668-678.
Patenaude, M. et al. Designing Injectable, Covalently Cross-Linked Hydrogels for Biomedical Applications. Macromol. Rapid Commun. 2014, 35:598-617.
Hsu, W-H et al. Thermosenstive Double Network of Zwitterionic Polyermers for Controlled Mechanical Strength of Hydrogels. RSC. Adv. 2019. 24241.

* cited by examiner

IN SITU GELLING ZWITTERIONIC HYDROGEL COMPOSITIONS, AND METHODS OF USE THEREOF

CROSS-REFERENCE TO RELATED APPLICATIONS

This application is a U.S. national stage filing under 35 U.S.C. § 371 from International Application No. PCT/CA2021/050731, filed on May 28, 2021, and published as WO2021/237369 on Dec. 2, 2021, which claims the benefit of priority to U.S. Provisional Application No. 63/031,169, filed May 28, 2020, the benefit of priority of each of which is claimed herein, and which applications and publications are hereby incorporated herein by reference in their entirety.

FIELD

The present application relates to hydrogel compositions comprising first and second precursor polymers, wherein the precursor polymers are zwitterionic copolymers that are crosslinked through electrophile-nucleophile bonds.

BACKGROUND

The prevention of nonspecific protein adsorption and microorganism attachment on material surfaces remains a challenge in many biological or engineering applications[1-4]. Nonspecific protein adsorption is considered as the first step to trigger the foreign-body reaction, which can inhibit the function of implanted biomaterials and induce tissue inflammation[5, 6]. Meanwhile, nonspecific biofouling on biosensor electrode interfaces negatively impacts their sensitivity and selectivity and limits their signal-to-noise ratios, leading to false signals and lower accuracy[7, 8]. Zwitterionic materials have emerged as promising ultra-low biofouling materials to resist nonspecific protein adsorption and limit cell and microbial adhesion across multiple applications, including biosensors, medical implanted devices wound healing, bioseparations, and others. The effective non-fouling properties of zwitterionic materials have been attributed to the combination of both cationic and anionic groups within each monomer residue[9, 10], resulting in extremely effective water binding to the materials and thus low fouling[11].

While many applications of zwitterionic polymers have focused on the fabrication of brushes or thin film surface coatings, the use of zwitterionic materials as building blocks for hydrogels has also attracted interest to exploit the functional properties of zwitterionic materials in bulk biomedical devices[1, 12]. However, most conventional preparations of zwitterionic hydrogels (typically via free radical copolymerization) result in elastic bulk hydrogels that cannot readily be injected, limiting their in vivo applications to invasive surgical procedures[13, 14].

Consequently, the development of injectable zwitterionic hydrogels that can be administered minimally invasively prior to gelling within the desired organ or tissue have attracted considerable attention[15, 16]. An effective in vivo-relevant injectable hydrogel platform should: (1) gel sufficiently slowly to allow for facile site-specific administration but sufficiently quickly that minimal diffusion of the pre-gel polymers occurs away from the target site; (2) facilitate the formation of physical and/or chemical crosslinks within the in vivo environment without any additional additive(s) or stimulus; and (3) degrade at an appropriate rate for the application into degradation products that can be cleared by the body[13, 15-20].

In situ-gelling polymers can also be beneficial for creating hydrogel-based coatings on other devices. In particular, covalent in situ-gelling hydrogels can impart benefits in terms of facilitating covalent anchoring of the coatings to the underlying surfaces as well as enabling the coatings to be applied via simple printing and/or dip-coating methods that do not require complex equipment or other additives[7, 11, 15, 21-32].

SUMMARY

The present disclosure relates to hydrogel compositions comprising precursor zwitterionic polymers which have been functionalized with either nucleophilic or electrophilic moieties. In one embodiment, the zwitterionic polymers are synthesized from [2-(methacryloyloxy)ethyl]dimethyl-(3-sulfopropyl)ammonium hydroxide (DMAPS) monomers to create functionalized polyDMAPS polymers. Mixing the functionalized precursor zwitterionic polymers directly leads to the formation of a hydrogel that exhibits anti-fouling, lubricious, and biocompatible properties while allowing the polymers to be injectable or printable and providing the additional benefit of mechanical and chemical tunability.

The present disclosure is directed to a hydrogel composition comprising:

a. at least one first precursor polymer which is a nucleophile-functionalized zwitterionic copolymer, and b. at least one second precursor polymer which is an electrophile-functionalized zwitterionic copolymer, wherein c. the first and second precursor polymers are crosslinked through covalent bonds.

In an embodiment, the present disclosure is directed to a hydrogel composition comprising:

a. a first precursor polymer which is a hydrazide-functionalized zwitterionic copolymer, and b. a second precursor polymer which is an aldehyde- and/or ketone-functionalized zwitterionic copolymer, wherein c. the first and second precursor polymers are crosslinked through hydrazone bonds.

Further, the present disclosure also includes a double-barrel syringe delivery method, comprising, a. a first precursor polymer which is a nucleophile-functionalized zwitterionic copolymer, and b. a second precursor polymer which is an electrophile-functionalized zwitterionic copolymer, wherein c. upon injection, the first and second precursor polymers form, in situ, the hydrogel composition.

DRAWING

The embodiments of the application will now be described in greater detail with reference to the attached drawings.

FIG. 1 is a schematic representation illustrating one example of the syntheses of zwitterionic precursor polymers, whereby the nucleophilic hydrazide copolymer is labeled ZH, and the electrophilic copolymers consisting of at least an aldehyde or a ketone moiety are labeled ZA, ZK, and ZK-co-A; these syntheses and structures are examples of the hydrogel composition of the disclosure.

FIG. 2 depicts an example of forming an injectable zwitterionic hydrogel of the disclosure through hydrolytically labile hydrazone bonds. In an embodiment, the injectable zwitterionic gels consist of a nucleophilic precursor copolymer (hydrazide, labeled ZH) and an electrophilic precursor copolymer (aldehyde, ketone, or ketone-co-aldehyde, labeled ZA, ZK, or ZK-co-A, respectively). Upon mixing, the copolymers create a tunable hydrazone crosslink while maintaining the zwitterionic properties.

FIG. 3 shows, in an embodiment, the various types of physical properties that can be achieved using hydrogels of the disclosure as a function of precursor degree of functionality. A) Equilibrium mass-based swelling ratio in 10 mM phosphate buffer saline, pH 7.4. B) Degradation kinetics in 100 mM HCl. C) Viscosity versus shear rate. D) Shear storage (solid) and loss (hollow) moduli. E) Compressive moduli.

FIG. 4 shows, in one embodiment, the tribological characteristics of zwitterionic hydrogels of the disclosure A) as a function of precursor degree of functionality and polymer concentration in solution and B) as a function of precursor degree of functionality at a constant polymer concentration over multiple cycles and C) in terms of the lubricity of an injectable zwitterionic hydrogel of the disclosure relative to an injectable hydrogel whose backbone is PEG-based (POEGMA) instead of DMAPS.

Figure 8:
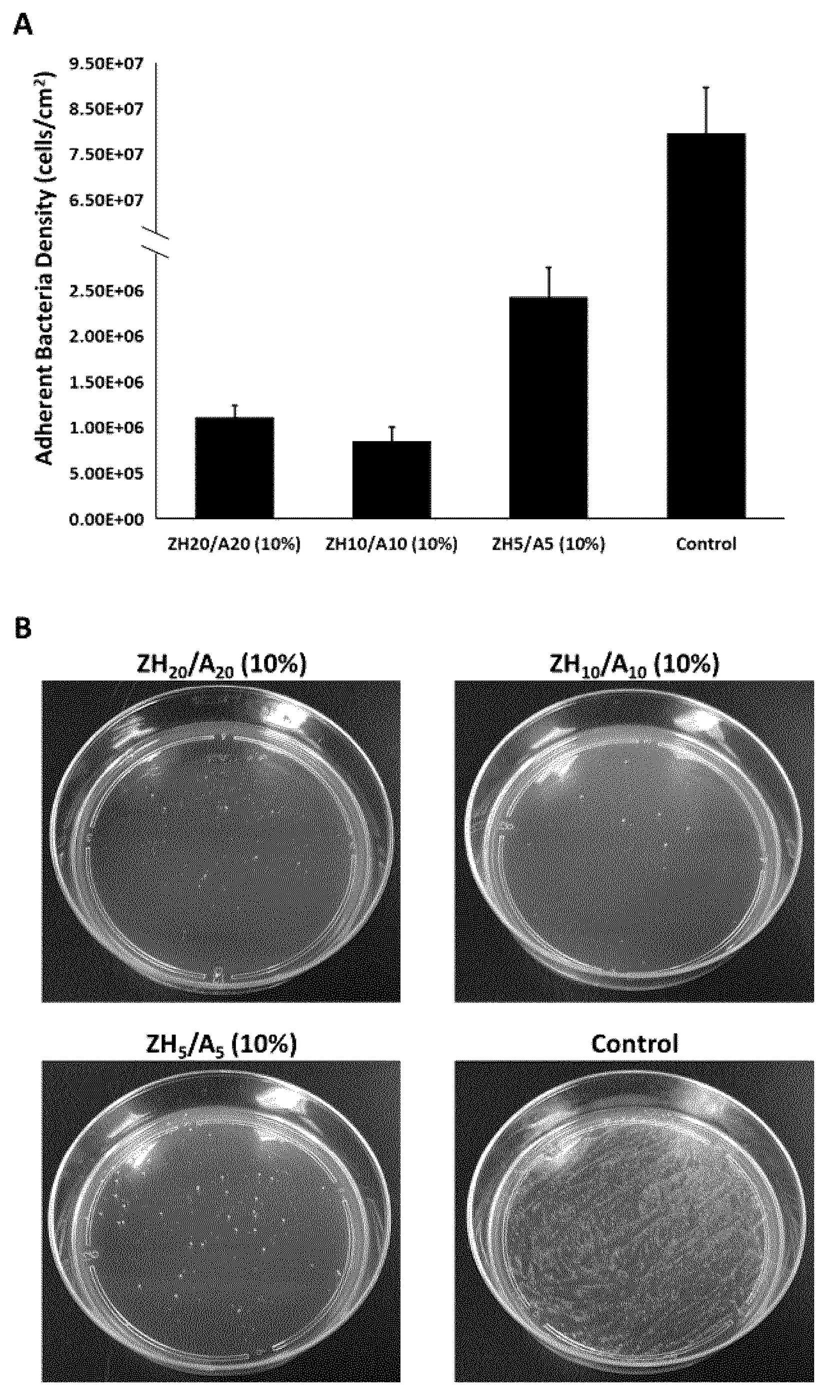

FIG. 8 shows bacterial surface adhesion of *E. coli* in one embodiment the disclosure. A) as a function of precursor degree of functionality. B) Images of *E. coli* colonies in agar plates after incubation and treatment of varying hydrogel formulations of the disclosure.

Figure 9:
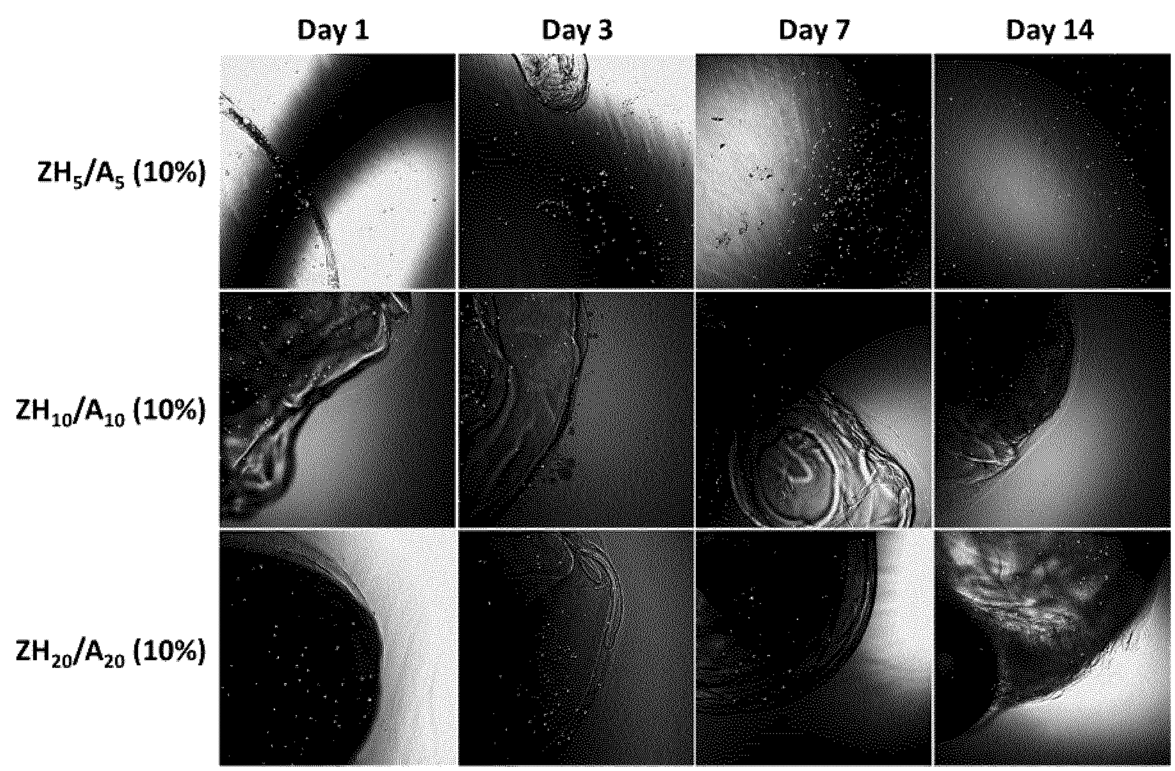

FIG. 9 shows the release of fluorescently labeled C2C12 mouse myoblasts in one embodiment of the disclosure as a function of precursor degree of functionality (rows) and time (columns) over a 14-day period.

Figure 10:
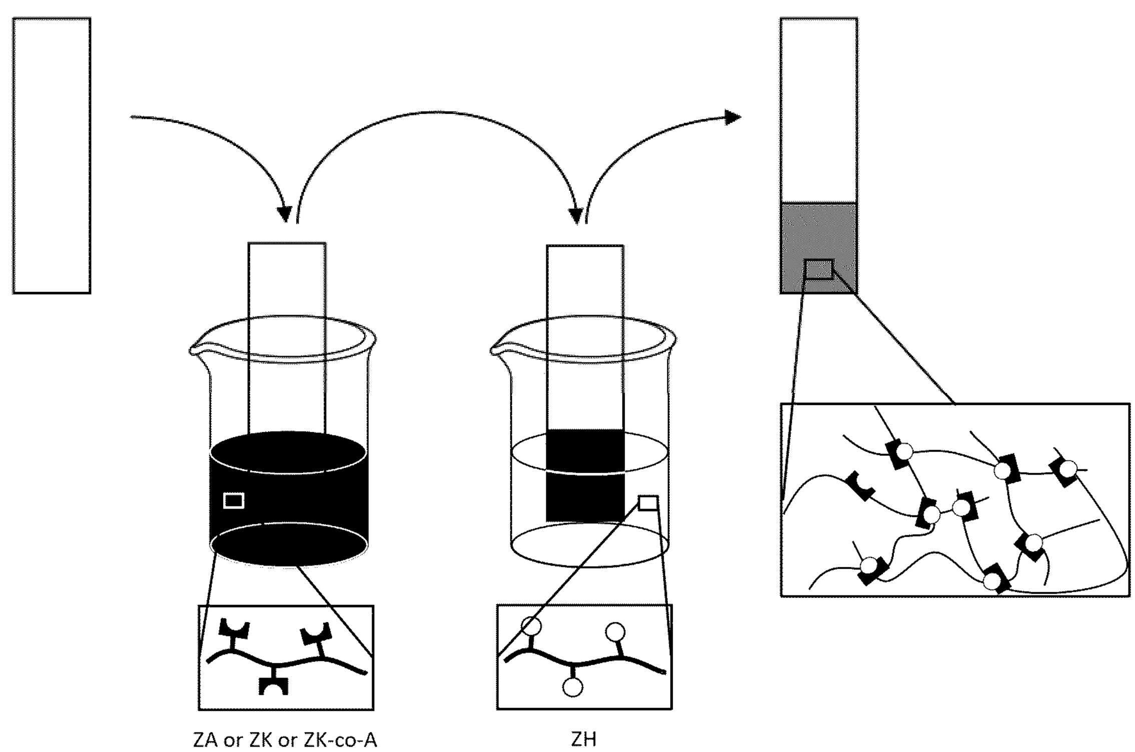

FIG. 10 shows the substrate dip-coating process in one embodiment of the disclosure.

Figure 11:
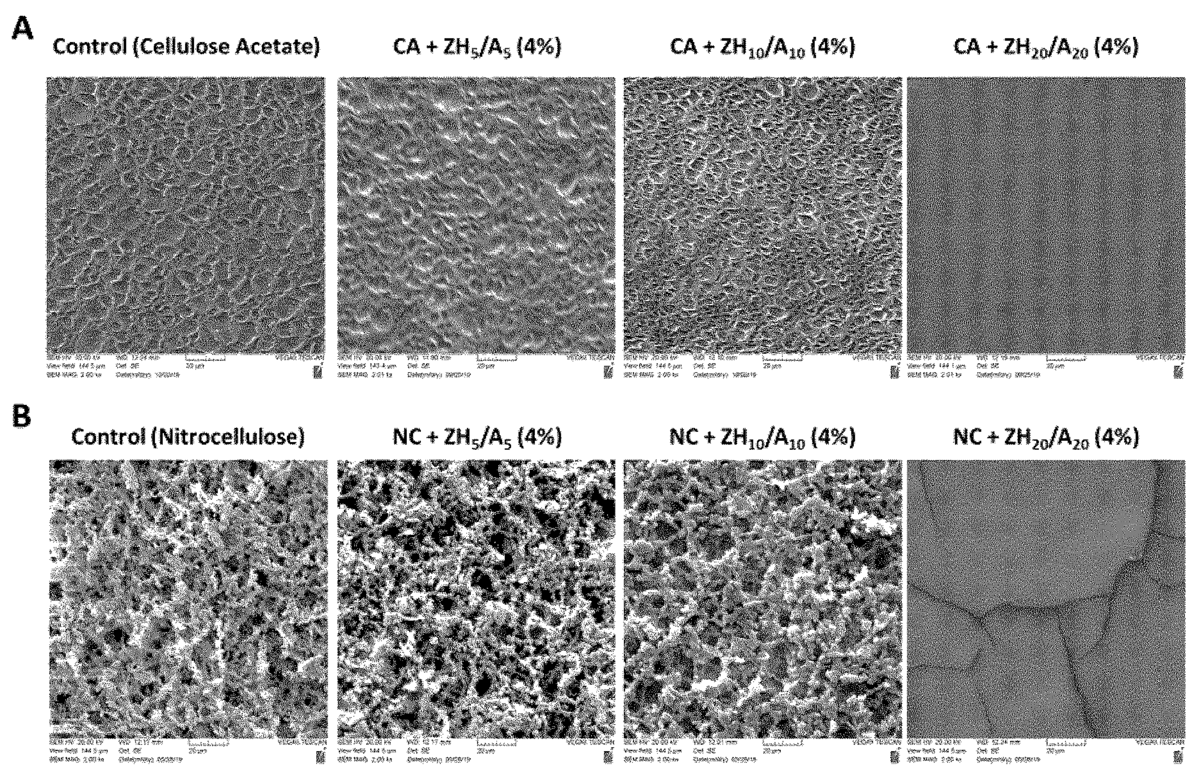

FIG. 11 shows scanning electron microscopy (SEM) images of native, and dip-coated cellulose-based membranes in one embodiment of the disclosure. A) cellulose acetate (CA) membranes, and B) nitrocellulose (NC) membranes, without modification compared to with one coat of varying polyDMAPS formulations.

Figure 12:
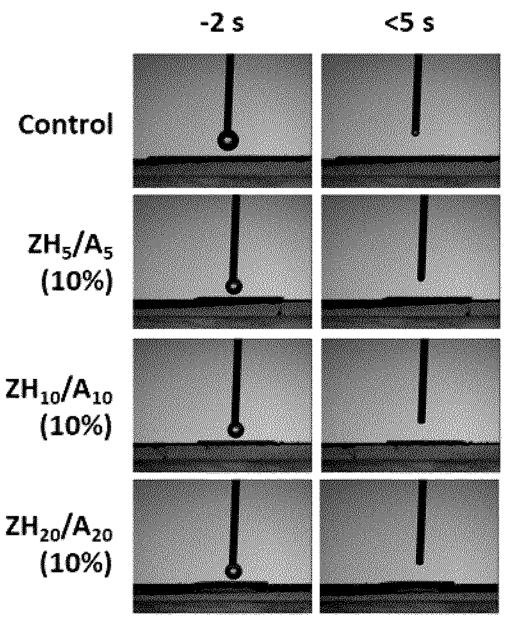
Figure 12:
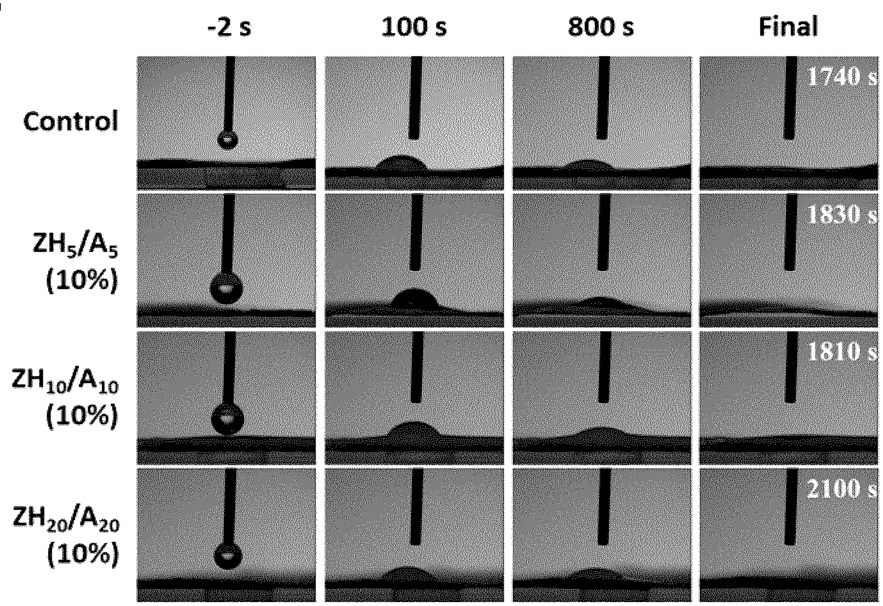

FIG. 12 shows the water contact angle and water droplet evolution over time for native and modified cellulose-based membranes with and without coating in one embodiment of the disclosure as a function of precursor degree of functionality. Each subsequent image in the same row tracks a single water droplet at the time period heading the column. A) cellulose acetate, B) nitrocellulose.

Figure 13:
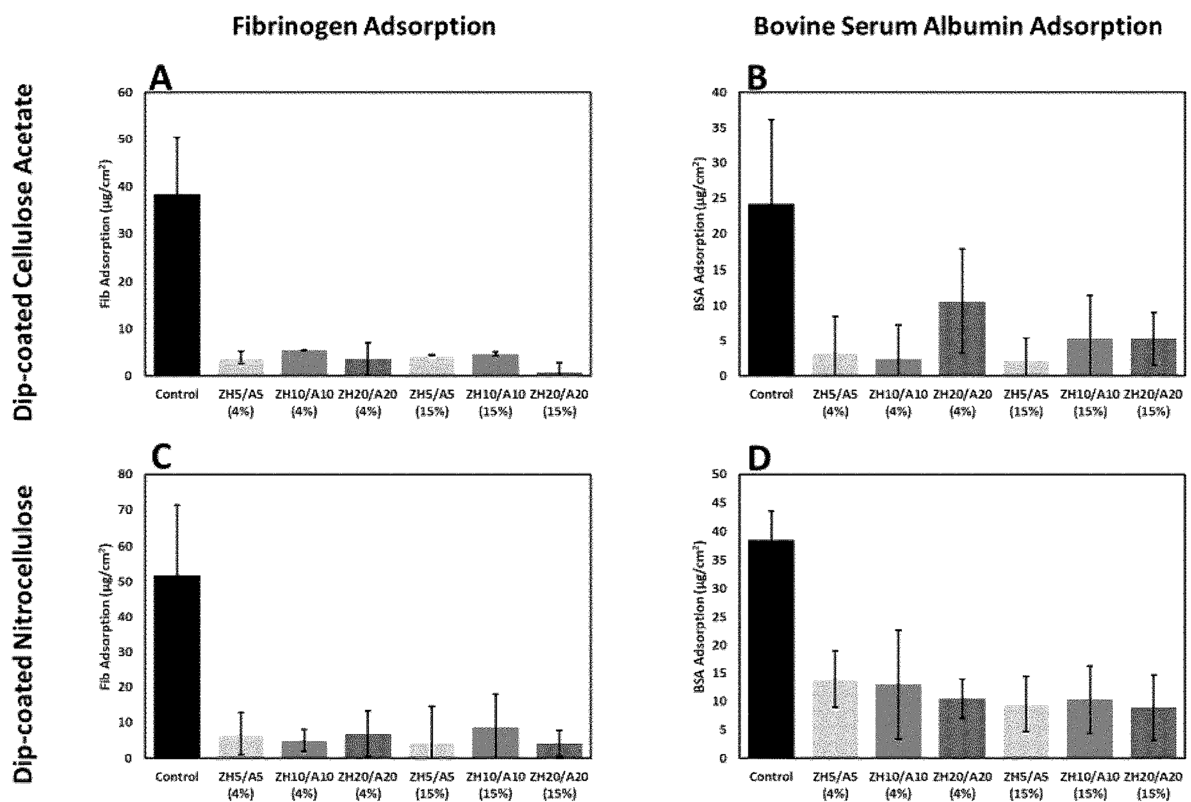

FIG. 13 shows the protein adsorption of bovine serum albumin (BSA) and fibrinogen (Fib) to cellulose-based membranes with and without coating of hydrogels in one embodiment of the disclosure as a function of precursor degree of functionality and protein concentration of BSA and Fib, respectively. A) Fib to cellulose acetate, B) BSA to cellulose acetate, C) Fib to nitrocellulose, D) BSA to nitrocellulose.

Figure 14:
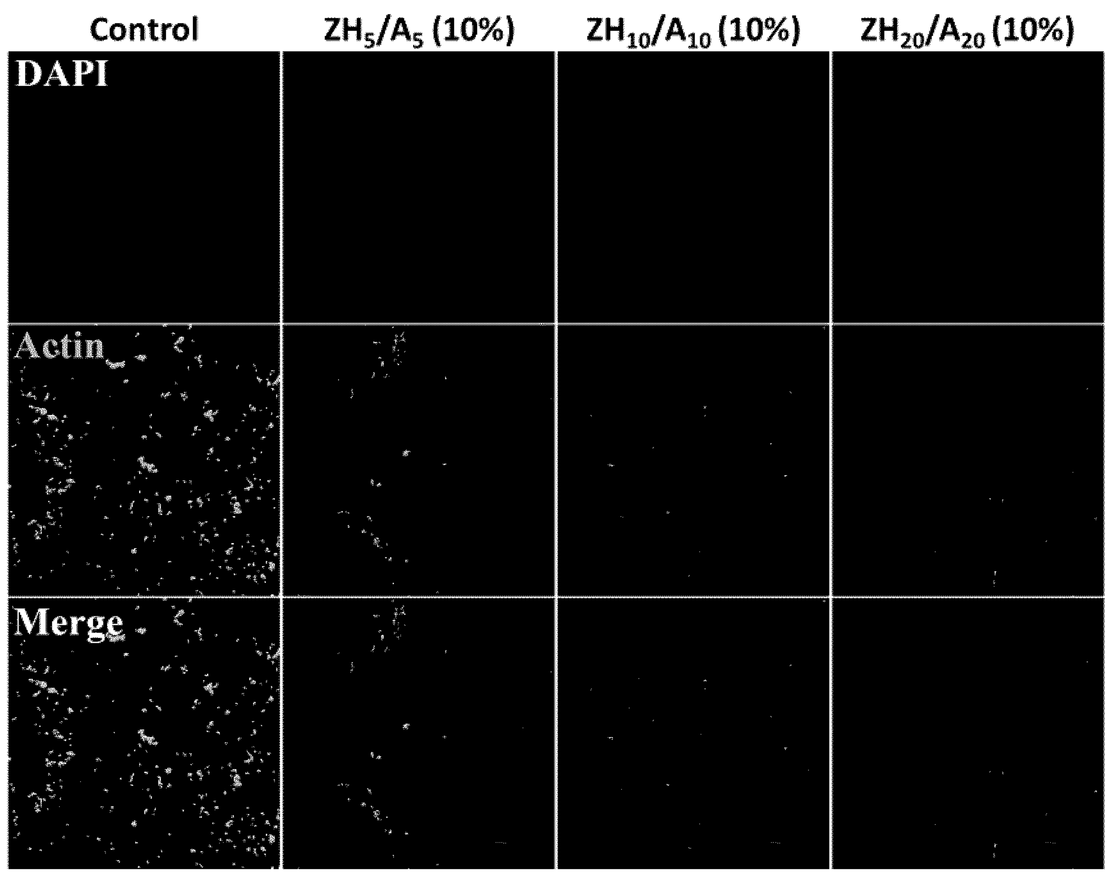

FIG. 14 shows the cell adhesion of labeled 3T3 mouse fibroblasts to native and modified cellulose acetate membranes with and without coating of hydrogels in one embodiment of the disclosure as a function of precursor functionality after 24 h.

Figure 15:
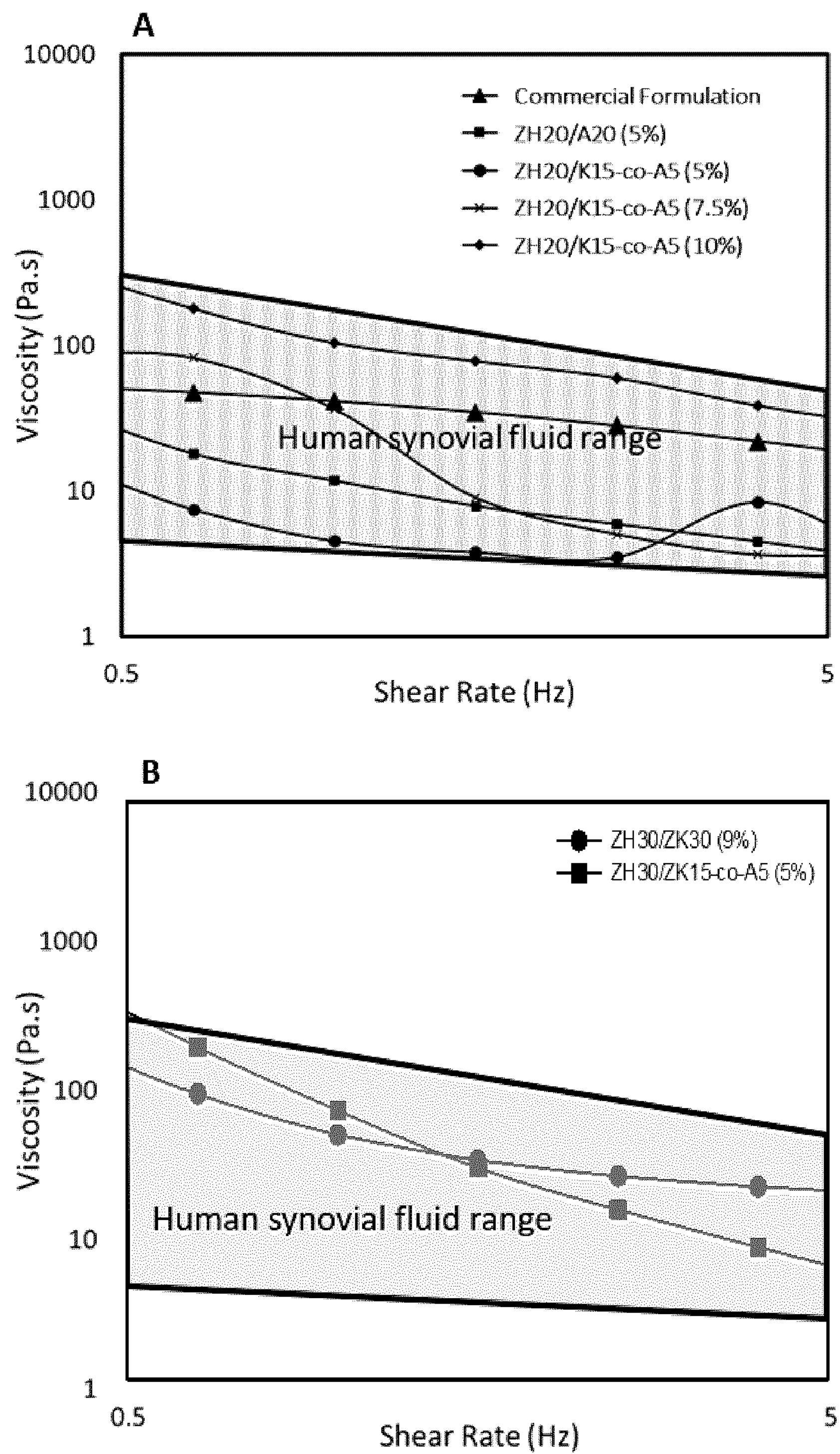

FIG. 15 shows the viscosity versus shear rate response of hydrogels in one embodiment of the disclosure in comparison to human synovial fluid and a commercial viscosupplement.

Figure 16:
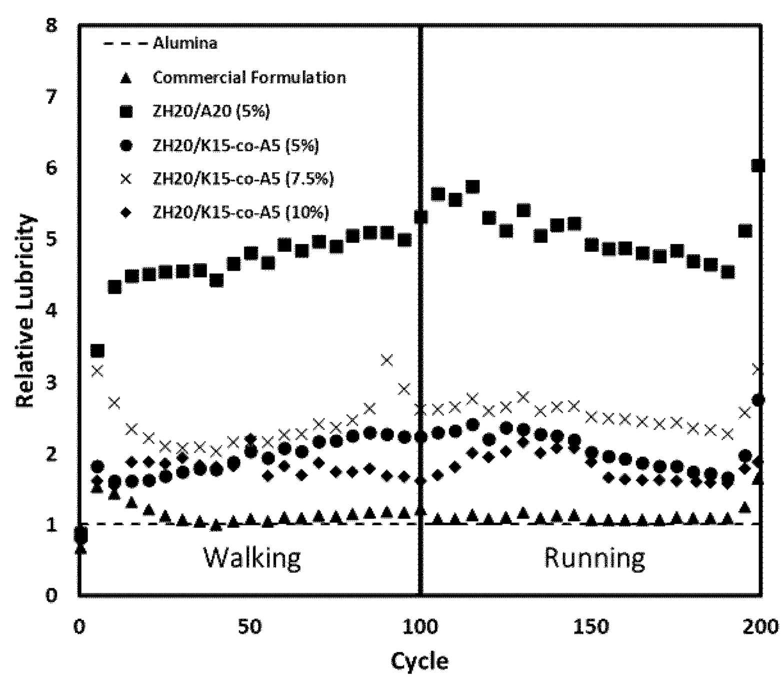

FIG. 16 shows the relative lubricity of hydrogels in comparison in one embodiment of the disclosure to a hard silica-alumina interface and a commercial viscosupplement.

Figure 17:
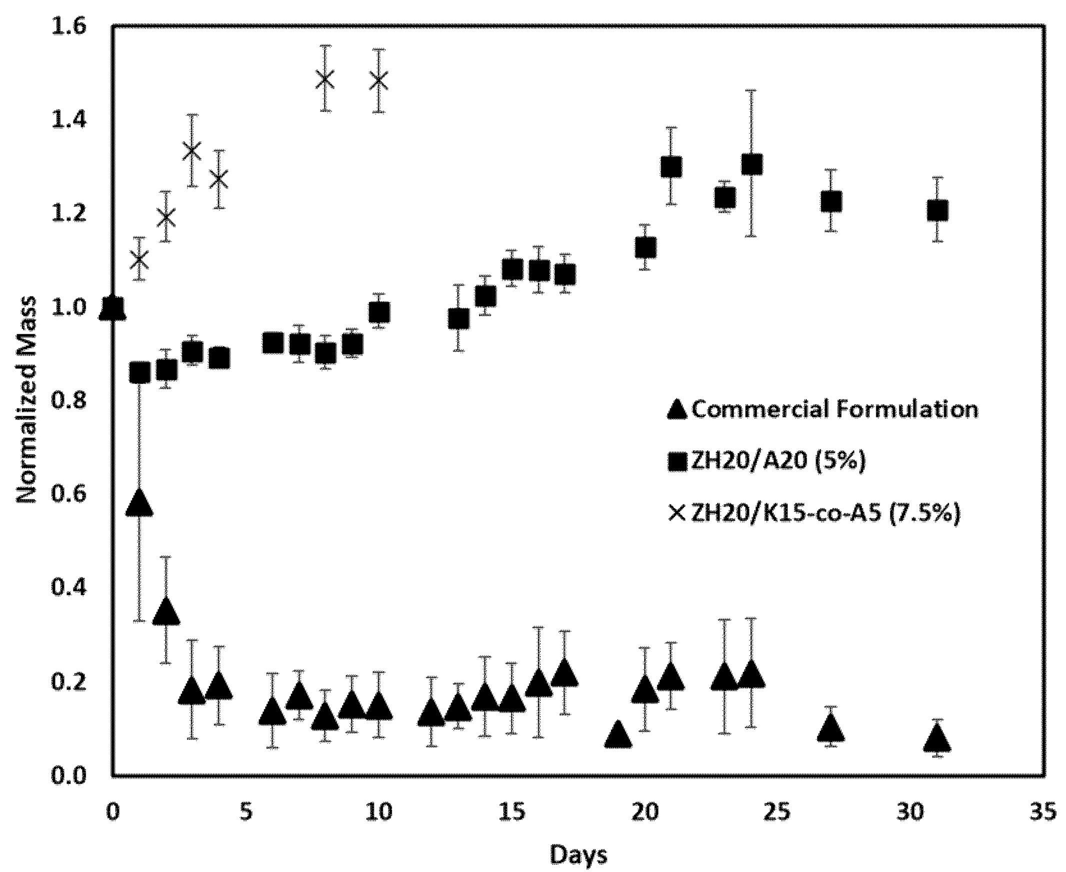

FIG. 17 shows the swelling and degradation properties of hydrogels in one embodiment of the disclosure in comparison to a commercial viscosupplement in the presence of synoviocyte culture media.

Figure 18:
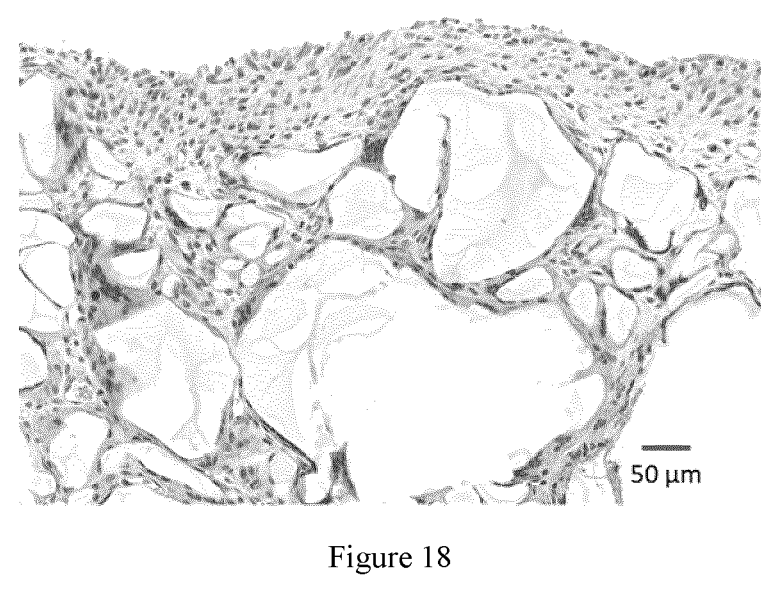

FIG. 18 shows a characteristic chronic tissue response to the subcutaneous injection of hydrogels in one embodiment of the disclosure.

DETAILED DESCRIPTION a. Definitions

Unless otherwise indicated, the definitions and embodiments described in this and other sections are intended to be applicable to all embodiments and aspects of the present application herein described for which they are suitable as would be understood by a person skilled in the art.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

As used in this application, the singular forms "a", "an" and "the" include plural references unless the content clearly dictates otherwise.

In embodiments comprising an "additional" or "second" component, the second component as used herein is chemically different from the other components or first component. A "third" component is different from the other, first, and second components, and further enumerated or "additional" components are similarly different.

The term "and/or" as used herein means that the listed items are present, or used, individually or in combination. In effect, this term means that "at least one of" or "one or more" of the listed items is used or present.

The term "suitable" as used herein means that the selection of the particular compound or conditions would depend on the specific synthetic manipulation to be performed, and the identity of the molecule(s) to be transformed, but the selection would be well within the skill of a person trained in the art. All process/method steps described herein are to be conducted under conditions sufficient to provide the product shown. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

The term "alkyl" as used herein, whether it is used alone or as part of another group, means straight or branched chain, saturated alkyl groups, and includes for example, methyl, ethyl, propyl, isopropyl, n-butyl, s-butyl, isobutyl, t-butyl, 2,2-dimethylbutyl, n-pentyl, 2-methylpentyl, 3-methylpentyl, 4-methylpentyl, n-hexyl and the like. The term $C_{1-6}$alkyl means an alkyl group having 1, 2, 3, 4, 5, or 6 carbon atoms.

The term "alkylene" as used herein, whether alone or as part of another group, means an alkyl group that is bivalent; i.e. that is substituted on two ends with another group. The term $C_{0-2}$alkylene means an alkylene group having 0, 1 or 2 carbon atoms. It is an embodiment of the application that, in the alkylene groups, one or more, including all, of the hydrogen atoms are optionally replaced with F or $^{2}H$.

The term "aryl" as used herein means a monocyclic, bicyclic or tricyclic aromatic ring system containing, depending on the number of atoms in the rings, for example from 6 to 10 carbon atoms, and at least 1 aromatic ring and includes, but is not limited to, phenyl, naphthyl, anthracenyl, 1,2-dihydronaphthyl, 1,2,3,4-tetrahydronaphthyl, fluorenyl, indanyl, indenyl and the like.

The term "heteroaryl" as used herein refers to cyclic groups that contain at least one aromatic ring and at least one heteroatom, such as N, O and/or S. The term $C_{5-10}$ heteroaryl means an aryl group having 5, 6, 7, 8, 9 or 10 atoms, in which at least one atom is a heteroatom, such as N, O and/or S, and includes, but is not limited to, thienyl, furyl, pyrrolyl, pyrididyl, indolyl, quinolyl, isoquinolyl, tetrahydroquinolyl, benzofuryl, benzothienyl and the like.

The term "polymerizable" as used herein refers to the property of individual monomers to react with other monomers, whether the same or different, under appropriate conditions to yield polymers.

The term "ethylenically unsaturated" as used herein refers to monomers having terminal, internal or pendant ethylenic unsaturation or any combination thereof and which can participate in a polymerization reaction. The ethylenic unsaturation may be a double or triple carbon-carbon bond The term "derivative" as used herein refers to a substance which comprises the same basic carbon skeleton and functionality as the parent compound, but can also bear one or more substituents or substitutions of the parent compound. For example, alkyl derivatives of sulfobetaine would include any compounds in which an alkyl group is substituted on the sulfobetaine backbone.

The term "precursor polymer" or "polymer" as used herein refers to a polymer or copolymer that has been modified to contain a reactive functional group, for example, a nucleophilic or electrophilic moiety. In one embodiment, a (precursor) polymer of the present disclosure comprises a hydrazide reactive group, or an aldehyde and/or ketone reactive functional group on a poly(sulfobetaine) polymer.

The term "copolymer" as used herein is defined as a polymer derived from two or more different monomers. In one embodiment, a copolymer of the present disclosure includes a co-polymer of 2-(methacryloloxy) ethyl] dimethyl-(3-sulfopropyl) ammonium hydroxide (DMAPS) and acrylic acid. Other co-polymers include, for example, a co-polymer of DMAPS and N-(2,2-dimethoxyethyl)methacrylamide (DMEMAm) and/or diacetone acrylamide (DiAAAm), allylic aldehyde, 2-(methacryloyloxy)ethyl acetoacetate (AAEM), and/or N-((2-methyl-1,3-dioxolan yl)methyl)methacrylamide (MDM).

The term "zwitterionic" refers to a monomer in which there is one cationic functional group and one anionic functional group in the same monomer unit, resulting in a zero net charge within the monomer, or a monomer residue within a polymer, at the specific pH value considered. For example, depending on pH, a zwitterionic moiety may not contain the cationic and anionic groups, but is still considered zwitterionic.

The term "nucleophile-functionalized" "or nucleophilic moiety" as used herein refers to a polymer or copolymer comprised of, for example, at least five repeating units in which a part of the polymer or copolymer has been functionalized with a nucleophilic moiety which can react with an electrophile or electrophilic moiety to form covalent cross-linked bonds.

The term "electrophile-functionalized" or "electrophilic moiety" as used herein refers to a polymer or copolymer comprised of, for example, at least five repeating units in which a part of the polymer or copolymer has been functionalized with an electrophilic moiety which can react with a nucleophile or nucleophilic moiety to form covalent cross-linked bonds.

The term "polymeric backbone" as used herein refers to the main chain of a suitable polymer comprising a series of covalently bonded atoms that together create the continuous chain (straight or branched) of the polymeric molecule.

The term "crosslinked" or "crosslink" as used herein is defined as a bond that links a first (precursor) polymer to a second (precursor) polymer. For example, the bonds can be covalent bonds. For example, the "crosslink" is a reversible hydrazone bond formed between a reactive hydrazide, and aldehyde and/or ketone functional groups.

The term "hydrogel" as used herein refers to a polymeric material that exhibits the ability to swell and retain a significant fraction of water within its structure, without dissolving in water.

The term "w/w" as used herein means the number of grams of solute in 100 g of solution.

The term "w/v" as used herein refers to the number of grams of solution in 100 mL of solvent.

The term "hydrocarbyl moiety" as used herein refers to an organic moiety which is aliphatic, and optionally containing O, N, NR, S, and/or P as substituents, or as moieties intervening in the parent hydrocarbyl chain, and therein the hydrocarbyl moiety is optionally substituted with —($C_1$-$C_6$)-alkyl groups such as methyl, ethyl, propyl, butyl.

ii. Synthesis of Materials

The present disclosure is generally directed to a hydrogel composition comprising a first precursor polymer, which is a nucleophile-functionalized zwitterionic copolymer and a second precursor polymer, which is an electrophile-functionalized zwitterionic copolymer, wherein the first and second precursor polymers are crosslinked through covalent bonds by reaction between the nucleophilic and electrophilic moieties. In one embodiment, the zwitterionic hydrogel compositions of the disclosure are chemically and mechanically tunable and also injectable.

The present disclosure includes a hydrogel composition, comprising a. a first polymer comprising monomeric units of
   i. one or more first polymerizable ethylenically unsaturated zwitterionic monomers containing at least one cationic charge and at least one anionic charge at the specific pH considered, for example neutral pH; and
   ii. one or more polymerizable ethylenically unsaturated monomers functionalized with a nucleophilic moiety;
b. a second polymer comprising monomeric units of
   i. one or more second polymerizable ethylenically unsaturated zwitterionic monomers containing at least one cationic charge and at least one anionic charge at the specific pH considered, for example neutral pH; and
   ii. one or more polymerizable ethylenically unsaturated monomer functionalized with an electrophilic moiety, wherein the first and second polymers are crosslinked through covalent bonds by reaction of the nucleophilic and electrophilic moieties to form the hydrogel composition.

In one embodiment, the first and second zwitterionic moieties independently or simultaneously have the structure

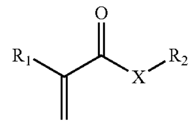

wherein

X is O or NR', wherein R' is H or $(C_1\text{-}C_6)$-alkyl;

$R_1$ is H, $(C_1\text{-}C_{10})$-alkyl, OH, or —O—$(CH_2)_x$ where x is an integer between 1 and 10;

$R_2$ is a hydrocarbyl moiety containing an anionic moiety and a cationic moiety.

In one embodiment, the hydrocarbyl moiety is a $C_1\text{-}C_{20}$-hydrocarbyl moiety, or $C_1\text{-}C_{10}$-hydrocarbyl, or $C_1\text{-}C_6$-hydrocarbyl moiety, wherein one or more carbon atoms in the moiety are optionally replaced with oxygen atoms, sulfur atoms (for, example a sulfate group) or nitrogen atoms (substituted with $C_1\text{-}C_6$-alkyl).

In another embodiment, the first and second zwitterionic moieties independently or simultaneously have the structure

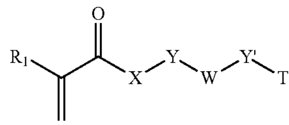

wherein

X is O or NR', wherein R' is H or $(C_1\text{-}C_6)$-alkyl;

$R_1$ is H, $(C_1\text{-}C_{10})$-alkyl, OH, or —O—$(CH_2)_x$ where x is an integer between 1 and 10;

Y and Y' are independently or simultaneously $(C_1\text{-}C_{10})$-alkylene, optionally wherein one or more carbon atoms are replaced with oxygen atoms;

W is a cationic moiety or an anionic moiety; and

T is an anionic moiety or a cationic moiety, wherein when W is a cationic moiety, T is an anionic moiety, and when W is an anionic moiety, T is a cationic moiety, and wherein the net charge of the monomer is zero at a specific pH of interest, for example neutral pH.

In another embodiment, the cationic moiety is an amine or ammonium moiety.

In another embodiment, the amine moiety is —NR'— and the ammonium moiety is —$N^+$R'R"—, wherein R' and R" are independently or simultaneously H or $(C_1\text{-}C_6)$-alkyl.

In another embodiment, the anionic moiety is a sulfate, carboxyl, phosphate, or boronate moiety.

In another embodiment, the first and second zwitterionic monomers independently or simultaneously have the structure

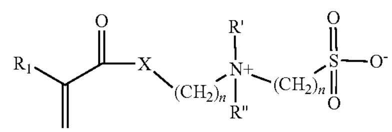

wherein,

X is O or NR', wherein R' is H or $(C_1\text{-}C_6)$-alkyl $R_1$ is H, $(C_1\text{-}C_{10})$-alkyl, OH, or —O—$(CH_2)_x$ where x is an integer between 1 and 10;

R' and R" are independently or simultaneously H or $(C_1\text{-}C_6)$-alkyl; and n is an integer from 1 to 10.

In one embodiment, the zwitterionic moiety has a net charge of zero, and depending on the pH, the cationic and anionic moieties may be neutral.

In another embodiment, the first and second zwitterionic monomers have the structure

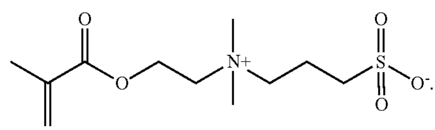

In another embodiment, the polymerizable ethylenically unsaturated monomer functionalized with a nucleophilic moiety has the formula

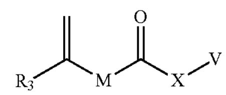

wherein

X is O or NR', wherein R' is H or $(C_1\text{-}C_6)$-alkyl;

$R_3$ is H or $(C_1\text{-}C_6)$-alkyl;

M is $(C_0\text{-}C_3)$-alkylene; and

V is a hydrocarbyl moiety containing a nucleophilic moiety.

In another embodiment, the polymerizable ethylenically unsaturated monomer functionalized with a nucleophilic moiety has the formula

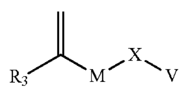

wherein

X is O or NR', wherein R' is H or $(C_1-C_6)$-alkyl;

$R_3$ is H or $(C_1-C_6)$-alkyl;

M is $(C_1-C_3)$-alkylene; and

V is a hydrocarbyl moiety containing a nucleophilic moiety

In one embodiment, the polymerizable ethylenically unsaturated monomer functionalized with a nucleophilic moiety has the formula

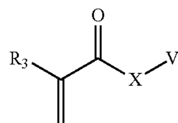

wherein

X is O or NR', wherein R' is H or $(C_1-C_6)$-alkyl;

$R_3$ is H or $(C_1-C_6)$-alkyl; and

V is a hydrocarbyl moiety containing a nucleophilic moiety.

In one embodiment, the hydrocarbyl moiety is a $C_1$-$C_{20}$-hydrocarbyl moiety, or $C_1$-$C_{10}$-hydrocarbyl, or $C_1$-$C_6$-hydrocarbyl moiety, wherein one or more carbon atoms in the moiety are optionally replaced with oxygen atoms, sulfur atoms (for, example a sulfate group) or nitrogen atoms (substituted with $C_1$-$C_6$-alkyl).

In one embodiment, the polymerizable ethylenically unsaturated monomer functionalized with a nucleophilic moiety has the formula

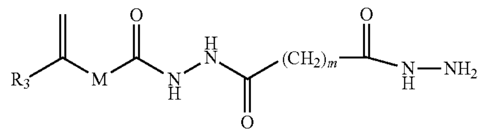

wherein m is 1-10, and $R_3$ is H or $CH_3$.

In one embodiment, the polymerizable ethylenically unsaturated monomer functionalized with a nucleophilic moiety has the formula

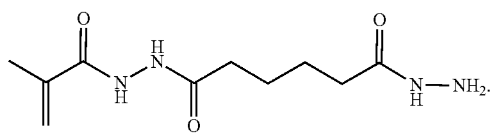 [SMILES: C=C(C)C(=O)NNC(=O)CCCCC(=O)NN]

In another embodiment, the polymerizable ethylenically unsaturated monomer functionalized with an electrophilic moiety has the formula

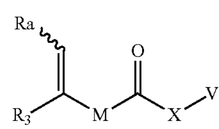

wherein

X is O or NR', wherein R' is H or $(C_1-C_6)$-alkyl;

Ra is H or —COOH;

$R_3$ is H or $(C_1-C_6)$-alkyl, wherein the $(C_1-C_6)$-alkyl group is optionally substituted with a —COOH group;

M is $(C_0-C_3)$-alkylene; and

V is a hydrocarbyl moiety containing at least one electrophilic moiety.

In one embodiment, the hydrocarbyl moiety is a $C_1$-$C_{20}$-hydrocarbyl moiety, or $C_1$-$C_{10}$-hydrocarbyl, or $C_1$-$C_6$-hydrocarbyl moiety, wherein one or more carbon atoms in the moiety are optionally replaced with oxygen atoms or nitrogen atoms (substituted with $C_1$-$C_6$-alkyl).

In one embodiment, the polymerizable ethylenically unsaturated monomer functionalized with an electrophilic moiety has the formula

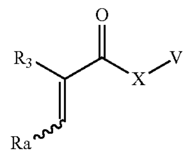

wherein

X is O or NR', wherein R' is H or $(C_1-C_6)$-alkyl;

Ra is H or —COOH;

$R_3$ is H or $(C_1-C_6)$-alkyl, wherein the $(C_1-C_6)$-alkyl group is optionally substituted with a —COOH group;

V is a hydrocarbyl moiety containing at least one electrophilic moiety.

In one embodiment, the hydrocarbyl moiety is a $C_1$-$C_{20}$-hydrocarbyl moiety, or $C_1$-$C_{10}$-hydrocarbyl, or $C_1$-$C_6$-hydrocarbyl moiety, wherein one or more carbon atoms in the moiety are optionally replaced with oxygen atoms, sulfur atoms (for, example a sulfate group) or nitrogen atoms (substituted with $C_1$-$C_6$-alkyl).

In one embodiment, the polymerizable ethylenically unsaturated monomer functionalized with an electrophilic moiety has the formula

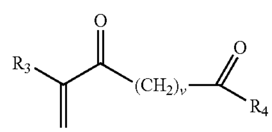

wherein $R_3$ is H or $(C_1-C_6)$-alkyl;

$R_4$ is H, $(C_1-C_{10})$-alkyl, wherein one or more $CH_2$ groups in $(C_1-C_{10})$-alkyl are replaced with C═O;

v is an integer from between 1 and 10; and wherein one or more carbon atoms in the group $(CH_2)_v$ are replaced with oxygen atoms or nitrogen atoms (NH or NR' wherein R' is $(C_1-C_6)$-alkyl).

In one embodiment, $R_4$ is $(C_1-C_6)$-alkyl, or $(C_1-C_3)$-alkyl, or methyl, ethyl, or propyl, wherein one $CH_2$ group in the alkyl group are replaced with C═O.

In another embodiment, the electrophilic monomers are 2-(methacryloyloxy)ethyl acetoacetate, diacetone acrylamide, allylic aldehyde, and/or N-((2-methyl-1,3-dioxolan-2-yl)methyl)methacrylamide.

In another embodiment, the nucleophilic moiety is a hydrazide or amine derivative, a carbonyl hydrate, an alcohol, cyanohydrin or cyanohydrin derivative, a thiol or thiol derivative, or a phosphorus ylide or derivatives thereof.

In another embodiment, the nucleophilic moiety is a hydrazide moiety.

In a further embodiment, the electrophilic moiety is an aldehyde, a ketone, a carboxylic acid, an ester, an amide, a maleimide, an acyl (acid) chloride, an acid anhydride or an alkene group or derivatives thereof.

In another embodiment, the electrophilic moiety is an aldehyde or ketone moiety.

In an embodiment, the first and second polymers are crosslinked via Michael addition, disulfides, imines, hydrazones, oximes, thioacetals, [2+4] Diels-Alder cycloaddition, and/or alkyne-azide chemistry In a further embodiment, the first and second polymers are crosslinked through hydrazone bonds.

In a further embodiment, the polymerizable ethylenically unsaturated monomer is derived from acrylic acid or a derivative thereof, methacrylic acid, itaconic acid, fumaric acid, maleic acid, or vinylacetic acid.

In another embodiment, the polymerizable ethylenically unsaturated monomer functionalized with an electrophilic moiety is N-(2,2-dimethoxyethyl)methacrylamide (DMEMAm), diacetone acrylamide, allylic aldehyde, 2-(methacryloyloxy)ethyl acetoacetate, and/or N-((2-methyl-1,3-dioxolan-2-yl)methyl)methacrylamide.

In another embodiment, the composition is used as an injectable biological lubricant or viscosupplement.

In a further embodiment, the composition is used as a coating for a substrate by a. adsorbing or reacting a first or second precursor polymer on the substrate;
b. coating the substrate with the alternate precursor polymer; and
c. optionally repeating steps (a) and (b).

In a further embodiment, the composition is used as an injectable delivery vehicle for cells by a. mixing living cells with one or more of the precursor polymers, and
b. co-extruding the copolymers to form an in situ hydrogel to encapsulate the cells.

The present disclosure also includes a method for the lubrication and/or viscosupplementation of a joint following the administration to the joint of a hydrogel composition of the disclosure.

In one embodiment, the subject is a human.

In another embodiment, the joint is a knee joint or hip joint.

In another embodiment, the joint is an arthritic joint or an osteoarthritic joint.

In another embodiment, the first and second polymers are intra-articularly injected into the joint of the subject and the hydrogel compositions forms in situ.

In another embodiment, the hydrogel further comprises a therapeutic agent that includes an antibody, a steroid, an anti-inflammatory agent, a growth factor, a peptide, or another agent suitable to treat a condition.

The present disclosure also includes a hydrogel composition, comprising a. a first polymer comprising monomeric units of
   i. one or more first polymerizable ethylenically unsaturated zwitterionic monomers containing at least one cationic charge and at least one anionic charge, at a specific pH of interest for example at neutral pH; and
   ii. one or more polymerizable ethylenically unsaturated monomers functionalized with a nucleophilic moiety;
b. a second polymer comprising monomeric units of
   i. one or more second polymerizable ethylenically unsaturated zwitterionic monomers containing at least one cationic charge and at least one anionic charge at a specific pH of interest for example at neutral pH; and
   ii. one or more polymerizable ethylenically unsaturated monomer functionalized with an electrophilic moiety, wherein the electrophilic moiety of at least one polymerizable ethylenically unsaturated monomer comprises a ketone group, a carboxylic acid, an ester, an amide, an acyl chloride, an acid anhydride, or an alkene group; and
   wherein the first and second polymers are crosslinked through covalent bonds by reaction of the nucleophilic and electrophilic moieties to form the hydrogel composition.

In one embodiment, at least one electrophilic moiety comprises a ketone group.

In one embodiment, at least one electrophilic moiety comprises a ketone group and a second polymer may further comprise monomers having an aldehyde, a ketone, a carboxylic acid, an ester, an amide, a maleimide, an acyl (acid) chloride, an acid anhydride or an alkene group or derivatives thereof.

In one embodiment, the first and second zwitterionic moieties independently or simultaneously have the structure

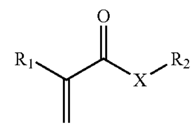

wherein

X is O or NR', wherein R' is H or $(C_1\text{-}C_6)$-alkyl;

$R_1$ is H, $(C_1\text{-}C_{10})$-alkyl, OH, or —O—$(CH_2)_x$ where x is an integer between 1 and 10;

$R_2$ is a hydrocarbyl moiety containing an anionic moiety and a cationic moiety.

In one embodiment, the hydrocarbyl moiety is a $C_1\text{-}C_{20}$-hydrocarbyl moiety, or $C_1\text{-}C_{10}$-hydrocarbyl, or $C_1\text{-}C_6$-hydrocarbyl moiety, wherein one or more carbon atoms in the moiety are optionally replaced with oxygen atoms, sulfur atoms (for, example a sulfate group) or nitrogen atoms (substituted with $C_1\text{-}C_6$-alkyl).

In another embodiment, the first and second zwitterionic moieties independently or simultaneously have the structure

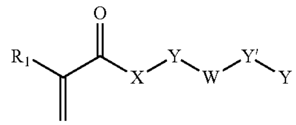

wherein

X is O or NR', wherein R' is H or $(C_1\text{-}C_6)$-alkyl;

$R_1$ is H, $(C_1\text{-}C_{10})$-alkyl, OH, or —O—$(CH_2)_x$ where x is an integer between 1 and 10;

Y and Y' are independently or simultaneously $(C_1\text{-}C_{10})$-alkylene, optionally wherein one or more carbon atoms are replaced with oxygen atoms;

W is a cationic moiety or an anionic moiety; and

T is an anionic moiety or a cationic moiety, wherein when W is a cationic moiety, T is an anionic moiety, and when W is an anionic moiety, T is a cationic moiety, and wherein the net charge of the monomer is zero at a specific pH of interest, for example neutral pH.

In one embodiment, $R_1$ is H, or $(C_1\text{-}C_6)$-alkyl, or methyl, ethyl or propyl.

In one embodiment, the cationic moiety is an amine or ammonium moiety.

In another embodiment, the amine moiety is —NR'— and the ammonium moiety is —N⁺R'R"—, wherein R' and R" are independently or simultaneously H or $(C_1\text{-}C_6)$-alkyl.

In another embodiment, the anionic moiety is a sulfate, carboxyl, phosphate, or boronate moiety.

In another embodiment, the first and second zwitterionic monomers independently or simultaneously have the structure

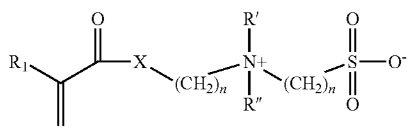

wherein,

X is O or NR', wherein R' is H or $(C_1\text{-}C_6)$-alkyl $R_1$ is H, $(C_1\text{-}C_{10})$-alkyl, OH, or —O—$(CH_2)_x$ where x is an integer between 1 and 10;

R' and R" are independently or simultaneously H or $(C_1\text{-}C_6)$-alkyl; and n is an integer from 1 to 10.

In a further embodiment, the first and second zwitterionic monomers have the structure

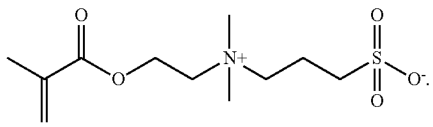

In another embodiment, the polymerizable ethylenically unsaturated monomer functionalized with a nucleophilic moiety has the formula

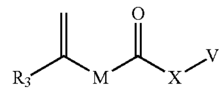

wherein

X is O or NR', wherein R' is H or $(C_1\text{-}C_6)$-alkyl;

$R_3$ is H or $(C_1\text{-}C_6)$-alkyl (or $(C_1\text{-}C_3)$-alkyl);

M is $(C_0\text{-}C_3)$-alkylene; and

V is a hydrocarbyl moiety containing a nucleophilic moiety.

In one embodiment, the hydrocarbyl moiety is a $C_1\text{-}C_{20}$-hydrocarbyl moiety, or $C_1\text{-}C_{10}$-hydrocarbyl, or $C_1\text{-}C_6$-hydrocarbyl moiety, wherein one or more carbon atoms in the moiety are optionally replaced with oxygen atoms, sulfur atoms (for, example a sulfate group) or nitrogen atoms (substituted with $C_1\text{-}C_6$-alkyl).

In a further embodiment, the polymerizable ethylenically unsaturated monomer functionalized with a nucleophilic moiety has the formula

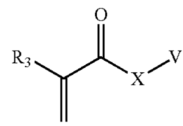

wherein

X is O or NR', wherein R' is H or $(C_1\text{-}C_6)$-alkyl;

$R_3$ is H or $(C_1\text{-}C_6)$-alkyl (or $(C_1\text{-}C_3)$-alkyl); and

V is a hydrocarbyl moiety containing a nucleophilic moiety.

In one embodiment, the hydrocarbyl moiety is a $C_1\text{-}C_{20}$-hydrocarbyl moiety, or $C_1\text{-}C_{10}$-hydrocarbyl, or $C_1\text{-}C_6$-hydrocarbyl moiety, wherein one or more carbon atoms in the moiety are optionally replaced with oxygen atoms, sulfur atoms (for, example a sulfate group) or nitrogen atoms (substituted with $C_1\text{-}C_6$-alkyl).

In one embodiment, the polymerizable ethylenically unsaturated monomer functionalized with a nucleophilic moiety has the formula

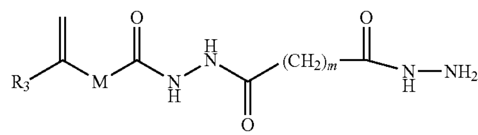

wherein m is 1-10, or 1, 2, 3, 4, 5, 6, 7, 8, 9 or 10.

In one embodiment, the polymerizable ethylenically unsaturated monomer functionalized with a nucleophilic moiety has the formula

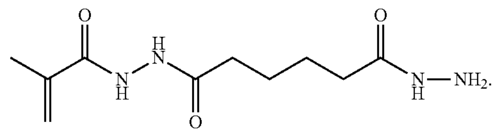 [SMILES: C=C(C)C(=O)NNC(=O)CCCCC(=O)NN]

In another embodiment, the polymerizable ethylenically unsaturated monomer functionalized with an electrophilic moiety has the formula

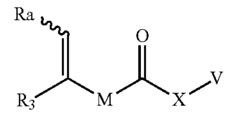

wherein

X is O or NR', wherein R' is H or $(C_1\text{-}C_6)$-alkyl;

Ra is H or —COOH;

$R_3$ is H or $(C_1\text{-}C_6)$-alkyl (or $(C_1\text{-}C_3)$-alkyl), wherein the $(C_1\text{-}C_6)$-alkyl group is optionally substituted with a —COOH group;

M is $(C_0\text{-}C_3)$-alkylene; and

V is a hydrocarbyl moiety containing at least one electrophilic moiety, wherein at least one electrophilic moiety comprises a ketone group.

In one embodiment, the hydrocarbyl moiety is a $C_1\text{-}C_{20}$-hydrocarbyl moiety, or $C_1\text{-}C_{10}$-hydrocarbyl, or $C_1\text{-}C_6$-hydrocarbyl moiety, wherein one or more carbon atoms in the moiety are optionally replaced with oxygen atoms, sulfur atoms (for, example a sulfate group) or nitrogen atoms (substituted with $C_1$-$C_6$-alkyl).

In one embodiment, polymerizable ethylenically unsaturated monomer functionalized with an electrophilic moiety has the formula

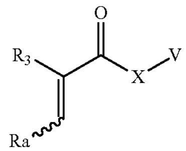

wherein

X is O or NR', wherein R' is H or ($C_1$-$C_6$)-alkyl;

Ra is H or —COOH;

$R_3$ is H or ($C_1$-$C_6$)-alkyl (or ($C_1$-$C_3$)-alkyl), wherein the ($C_1$-$C_6$)-alkyl group is optionally substituted with a —COOH group;

V is a hydrocarbyl moiety containing at least one electrophilic moiety, wherein at least one electrophilic moiety comprises a ketone group.

In one embodiment, the hydrocarbyl moiety is a $C_1$-$C_{20}$-hydrocarbyl moiety, or $C_1$-$C_{10}$-hydrocarbyl, or $C_1$-$C_6$-hydrocarbyl moiety, wherein one or more carbon atoms in the moiety are optionally replaced with oxygen atoms, sulfur atoms (for, example a sulfate group) or nitrogen atoms (substituted with $C_1$-$C_6$-alkyl).

In one embodiment, the polymerizable ethylenically unsaturated monomer functionalized with an electrophilic moiety has the formula

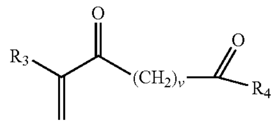

wherein $R_3$ is H or ($C_1$-$C_6$)-alkyl (or ($C_1$-$C_3$)-alkyl);

$R_4$ is H, ($C_1$-$C_{10}$)-alkyl, wherein one or more $CH_2$ groups in ($C_1$-$C_{10}$)-alkyl are optionally replaced with C═O;

v is an integer from between 1 and 10; and wherein one or more carbon atoms in the group $(CH_2)_v$ are optionally replaced with oxygen atoms or nitrogen atoms (NH or NR' wherein R' is $C_1$-$C_6$-alkyl).

In one embodiment, $R_4$ is ($C_1$-$C_6$)-alkyl, or ($C_1$-$C_3$)-alkyl, or methyl, ethyl, or propyl, wherein at least one $CH_2$ group in the alkyl group is replaced with C═O.

In one embodiment, when the electrophilic moiety is a ketone, $R_4$ cannot be H. In another embodiment, a second electrophilic moiety is an aldehyde group and $R_4$ is H or ($C_1$-$C_{10}$)-alkyl, wherein the terminal $CH_2$ group in ($C_1$-$C_{10}$)-alkyl is optionally replaced with C═O to form an aldehyde.

In one embodiment, the ketone functionality is optionally derived from another group as, for example, an acetal, such as a cyclic acetal. For example, —C(═O)—$CH_3$ can be present as

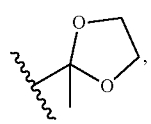 [SMILES: *C1(C)OCCO1]

and converted to —C(═O)—$CH_3$ after hydrolysis.

In one embodiment, the polymerizable ethylenically unsaturated monomer functionalized with an electrophilic moiety has the formula

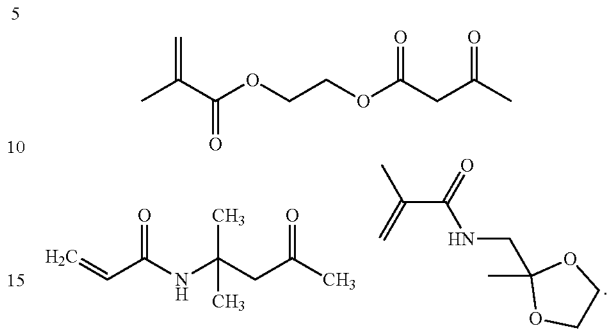

In one embodiment, the nucleophilic moiety is a hydrazide or amine derivative, a carbonyl hydrate, an alcohol, cyanohydrin or cyanohydrin derivative, a thiol or thiol derivative, or a phosphorus ylide or derivatives thereof.

In another embodiment, the nucleophilic moiety is a hydrazide moiety.

In one embodiment, at least one electrophilic moiety comprises a ketone group, and the second polymer may further comprise monomers having an aldehyde, a ketone, a carboxylic acid, an ester, an amide, a maleimide, an acyl (acid) chloride, an acid anhydride or an alkene group or derivatives thereof.

In one embodiment, the second polymer comprises both an aldehyde moiety and a ketone moiety.

In one embodiment, the first and second polymers are crosslinked through hydrazone bonds.

In another embodiment, the polymerizable ethylenically unsaturated monomer is derived from acrylic acid or a derivative thereof, methacrylic acid, itaconic acid, fumaric acid, maleic acid, or vinylacetic acid.

In one embodiment, the polymerizable ethylenically unsaturated monomer functionalized with an electrophilic moiety is N-(2,2-dimethoxyethyl)methacrylamide, N-((2-methyl-1,3-dioxolan-2-yl)methyl)methacrylamide, diacetone acrylamide, allylic aldehyde, or 2-(methacryloyloxy) ethyl acetoacetate.

In another embodiment, the disclosure includes a hydrogel composition, comprising a. at least one first precursor polymer which is a nucleophile-functionalized zwitterionic copolymer, and b. at least one second precursor polymer which is an electrophile-functionalized zwitterionic copolymer, wherein the first and second precursor polymers are crosslinked through covalent bonds by reaction of the nucleophilic and electrophilic moieties.

In one embodiment, the nucleophile-functionalized zwitterionic copolymer comprises a nucleophilic moiety which is a hydrazide or amine derivative, a carbonyl hydrate, an alcohol, cyanohydrin or cyanohydrin derivative, a thiol or thiol derivative, or a phosphorus ylide or derivatives thereof.

In one embodiment, the nucleophilic moiety is a hydrazide moiety.

In one embodiment, the electrophile-functionalized zwitterionic copolymer comprises an electrophilic moiety which is an aldehyde, a ketone, a carboxylic acid, an ester, an amides, a maleimide, an acyl (acid) chloride, an acid anhydride or an alkene group or derivatives thereof.

In one embodiment, the electrophilic moiety is an aldehyde or ketone moiety.

In one embodiment, the composition comprises a. at least one first precursor polymer which is a hydrazide-functionalized zwitterionic copolymer, and b. at least one second precursor polymer which is an aldehyde- and/or ketone-functionalized zwitterionic copolymer, wherein the first and second precursor polymers are crosslinked through hydrazone bonds.

In one embodiment, the first precursor polymer is a copolymer comprising monomeric units of:

a. a first monomer which is zwitterionic; and b. at least one second polymerizable monomer which is functionalized or is capable of being functionalized with a hydrazide moiety.

In one embodiment, the first monomer has the structure of the formula (I)

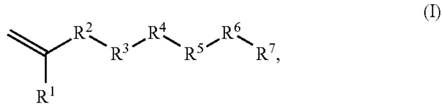

(I)

wherein

R1 is H, $(C_1\text{-}C_{10})$alkyl, OH, $O(CH_2)_xH$ in which x ranges between 1 to 10, or any functional group that does not substantially impair polymerization;

R2 is an ester (acrylic, methacrylic), an amide (acrylamido, methacrylamido), an alkyl group (allylic), an aromatic group (styrenic), or not present (vinylic);

R3 is $(C_1\text{-}C_{10})$alkyl, alkyl ether, or another hydrocarbyl moiety;

R4 is either a cationic component wherein the cationic component is an amine or ammonium functionality, or an anionic component wherein the anionic component is a sulfate, carboxyl, phosphate, or boronate functionality;

R5 is $(C_1\text{-}C_{10})$alkyl, alkyl ether, or another hydrocarbyl moiety;

R6 is a charged group selected from the list in R4 but of the opposite charge of R4;

R7 is H, $(C_1\text{-}C_{10})$alkyl, $(C_2\text{-}C_{10})$alkynyl, —$(C_0\text{-}C_4)$-alkylene-$(C_6\text{-}C_{10})$aryl, —$(C_0\text{-}C_4)$-alkylene-$(C_5\text{-}C_{10})$ ¬heteroaryl, —C(O)NR' or —C(O)OR', wherein R' is H or $(C_1\text{-}C_6)$alkyl, and n is any integer between 6 and 30, and the net charge of the monomer is zero at a specific pH of interest, for example neutral pH.

In one embodiment, the second polymerizable monomer has a carboxylic acid moiety.

In one embodiment, the second polymerizable monomer is acrylic acid or a derivative thereof, methacrylic acid, itaconic acid, fumaric acid, maleic acid, or vinylacetic acid.

In one embodiment, the first or second precursor polymers further comprise a third monomer.

In one embodiment, the second precursor polymer is a copolymer comprising monomeric units of:

a. a first monomer which is zwitterionic; and b. at least one second polymerizable monomer which can be functionalized with an aldehyde moiety and/or a ketone moiety.

In one embodiment, the first monomer has the structure of the formula (I)

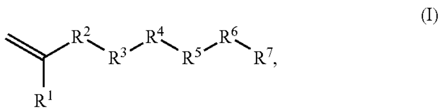

(I)

wherein

R1 is H, $(C_1\text{-}C_{10})$alkyl, OH, $O(CH_2)_xH$ in which x ranges between 1 to 10, or any functional group that does not substantially impair polymerization;

R2 is an ester (acrylic, methacrylic), an amide (acrylamido, methacrylamido), an alkyl group (allylic), an aromatic group (styrenic), or not present (vinylic);

R3 is $(C_1\text{-}C_{10})$alkyl, alkyl ether, or another hydrocarbyl moiety;

R4 is either a cationic component wherein the cationic component is an amine or ammonium functionality, or an anionic component wherein the anionic component is a sulfate, carboxyl, phosphate, or boronate functionality;

R5 is $(C_1\text{-}C_{10})$alkyl, alkyl ether, or another hydrocarbyl moiety;

R6 is a charged group selected from the list in R4 but of the opposite charge of R4;

R7 is H, $(C_1\text{-}C_{10})$alkyl, $(C_2\text{-}C_{10})$alkynyl, —$(C_0\text{-}C_4)$-alkylene-$(C_6\text{-}C_{10})$aryl, —$(C_0\text{-}C_4)$-alkylene-$(C_5\text{-}C_{10})$ ¬heteroaryl, —C(O)NR' or —C(O)OR', wherein R' is H or $(C_1\text{-}C_6)$alkyl, and n is any integer between 6 and 30, and the net charge of the monomer is zero at a specific pH of interest, for example neutral pH.

In one embodiment, the second polymerizable monomer is functionalized with an acetal moiety or a ketal moiety.

In another embodiment, the second polymerizable monomer is N-(2,2-dimethoxyethyl)methacrylamide, N-((2-methyl-1,3-dioxolan-2-yl)methyl)methacrylamide, diacetone acrylamide, allylic aldehyde, and/or 2-(methacryloyloxy)ethyl acetoacetate.

In another embodiment, the precursor polymers further comprises a third monomer which is acrylic acid, methacrylic acid, itaconic acid, fumaric acid, maleic acid, vinylacetic acid or tert-butyl-2-acryloylhydrazinecarboxylate (BAHC), N,N-dimethylaminoethyacrylate (DMAEA), aminoethyl methacrylate (AEMA), allylamine, diacetone acrylamide, allylic aldehyde, 2-(methacryloyloxy)ethyl acetoacetate, N-((2-methyl-1,3-dioxolan-2-yl)methyl) methacrylamide, or derivatives of any of the above.

In one embodiment, there is included a. the first precursor polymer is a co-polymer of at least one zwitterionic monomer and acrylic acid;

b. the second precursor polymer is a co-polymer of at least one zwitterionic monomer and N-(2,2-dimethoxyethyl) methacrylamide (DMEMAm), 2-(methacryloyloxy) ethyl acetoacetate (AAEM), diacetone acrylamide (DiAAAm), allylic aldehyde, and/or N-((2-methyl-1,3-dioxolan-2-yl)methyl)methacrylamide (MDM)

wherein acrylic acid has carboxylic acid groups which are functionalized as hydrazide moieties, and N-(2,2-dimethoxyethyl)methacrylamide has acetal groups which are converted to aldehyde moieties, and 2-(methacryloyloxy) ethyl acetoacetate, diacetone acrylamide, and/or N-((2-methyl-1,3-dioxolan-2-yl)methyl)methacrylamide have ketone moieties or can be converted to have ketone moieties, and hydrazone bonds form between the hydrazide and aldehyde or ketone moieties.

In one embodiment, the composition is used as an injectable biological lubricant or viscosupplement.

In another embodiment, the composition is used as a coating for a substrate by a. adsorbing or reacting a first or second precursor polymer on the substrate;
b. coating the substrate with the alternate precursor polymer; and
c. optionally repeating steps (a) and (b).

In another embodiment, the composition is used as an injectable delivery vehicle for cells by a. mixing living cells with one or more of the precursor polymers, and
b. co-extruding or otherwise mixing the copolymers to form an in situ-gelling hydrogel to encapsulate the cells.

Accordingly, the present disclosure is directed to a hydrogel composition comprising, a. at least one first precursor polymer which is a nucleophile-functionalized zwitterionic copolymer, and
b. at least one second precursor polymer which is an electrophile-functionalized zwitterionic copolymer, wherein the first and second precursor polymers are crosslinked through covalent bonds by reaction between the nucleophilic and electrophilic moieties.

In another embodiment, the nucleophile-functionalized zwitterionic copolymer comprises a nucleophilic moiety which is a hydrazine or amine derivative, a carbonyl hydrate, an alcohol, cyanohydrin or cyanohydrin derivative, a thiol or thiol derivative, or a phosphorus ylide or derivative thereof. In another embodiment, the nucleophilic moiety is a hydrazide.

In another embodiment, the electrophile-functionalized zwitterionic copolymer comprises an electrophilic moiety which is an aldehyde, a ketone, a carboxylic acid, an ester, an amide, a maleimide, an acyl (acid) chloride, an acid anhydride, or an alkene or derivatives thereof. In another embodiment, the electrophilic moiety is an aldehyde or a ketone.

In another embodiment, the hydrogel composition comprises two or more first precursor polymers. In another embodiment, the hydrogel composition comprises two or more second precursor polymers.

In another embodiment, the present disclosure is directed to a hydrogel composition, comprising, a. at least one first precursor polymer which is a hydrazide-functionalized zwitterionic copolymer, and
b. a second precursor polymer which is an aldehyde- and/or ketone-functionalized zwitterionic copolymer, wherein the first and second precursor polymers are crosslinked through hydrazone bonds.

In an embodiment, the first and second precursor polymers have a molecular weight which is less than the molecular weight cut-off for renal (kidney) clearance. In another embodiment, the first and second precursor polymers have a molecular weight which is less than about 70 kDa, or less than about 60 kDa. In another embodiment, the first and second precursor polymers have a molecular weight of about 10 kDa to about 60 kDa, or about 20 kDa to about 50 kDa.

In one embodiment, the first precursor polymer is a copolymer comprising monomeric units of:

a. a first monomer which is zwitterionic; and
b. at least one second polymerizable monomer which is functionalized, or is capable of being functionalized, with a nucleophilic moiety.

In an embodiment, the first monomer has the structure of the formula (I)

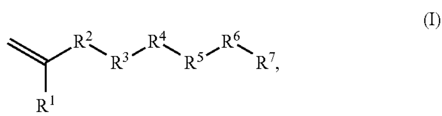

wherein

R1 is H, (C1-C10¬)alkyl, OH, $O(CH_2)_xH$ in which x ranges between 1 to 10, or any functional group that does not substantially impair polymerization.

R2 is an ester (acrylic, methacrylic), an amide (acrylamido, methacrylamido), an alkyl group (allylic), an aromatic group (styrenic), or not present (vinylic)

R3 is (C1-C10)alkyl, alkyl ether, or another hydrocarbyl moiety;

R4 is either a cationic component wherein the cationic component is an amine or ammonium functionality, or an anionic component wherein the anionic component is a sulfate, carboxyl, phosphate, or boronate functionality;

R5 is (C1-C10)alkyl, alkyl ether, or another hydrocarbyl moiety;

R6 is a charged group selected from the list in R4 but of the opposite charge of R4;

R7 is H, (C1-C10¬)alkyl, (C2-C10¬)alkynyl, —(C0-C4)-alkylene-(C6-C10¬)aryl, —(C0-C4)-alkylene-(C5-C10)¬heteroaryl, —C(O)NR' or —C(O)OR', wherein R' is H or (C1-C6)alkyl, and n is any integer between 6 and 30, and the net charge of the monomer is zero at a specific pH of interest, for example neutral pH.

In another embodiment, the second polymerizable monomer is functionalized, or is capable of being functionalized, with at least one nucleophilic moiety, wherein the nucleophilic moiety is hydrazine or amine derivative, a carbonyl hydrate, an alcohol, cyanohydrin or cyanohydrin derivative, a thiol or thiol derivative, or a phosphorus ylide or derivatives thereof. In another embodiment, the nucleophilic moiety is a hydrazide.

In another embodiment, the first precursor polymer is a copolymer comprising monomeric units of:

a. a first monomer which is zwitterionic; and
b. at least one second polymerizable monomer which is functionalized, or is capable of being functionalized, with a hydrazide moiety.

In one embodiment, the second polymerizable monomer has a carboxylic acid moiety, as the carboxylic acid can be functionalized to a hydrazide moiety. In another embodiment, the second polymerizable monomer is acrylic acid or a derivative thereof, methacrylic acid, itaconic acid, fumaric acid, maleic acid, or vinylacetic acid. In a further embodiment, the second monomer is acrylic acid or a derivative thereof. In another embodiment, the second polymerizable moiety is vinyl alcohol or allylic alcohol, which can be functionalized to a hydrazide moiety. In another embodiment, the second polymerizable moiety contains a nucleophilic moiety, such as a hydrazide moiety. In one embodiment, the second polymerizable moiety is acrylic acid functionalized with a hydrazide moiety.

In another embodiment of the disclosure, the first precursor polymer is a co-polymer which further comprises three or more monomers that can be co-polymerized with the zwitterionic monomer and the functional monomer.

In another embodiment of the disclosure, the second precursor polymer is a copolymer comprising monomeric units of:

a. a first monomer which is zwitterionic; and b. at least one polymerizable monomer which is functionalized, or is capable of being functionalized, with an electrophilic moiety.

In another embodiment, the second polymerizable monomer is functionalized, or is capable of being functionalized, with one or more electrophilic moiet(ies), wherein the electrophilic moiet(ies) are an aldehyde, a ketone, a carboxylic acid, an ester, an amide, a maleimide, an acyl (acid) chloride, an acid anhydride, or an alkene or derivatives thereof. In another embodiment, the electrophilic moieties are an aldehyde and/or a ketone moiety.

In an embodiment, the second precursor polymer is a copolymer comprising monomeric units of:

a. a first monomer which is zwitterionic;

b. a second polymerizable monomer which is functionalized, or is capable of being functionalized, with an electrophilic moiety, wherein the electrophilic moiety is an aldehyde; and c. a third polymerizable monomer which is functionalized, or is capable of being functionalized with an electrophilic moiety, wherein the electrophilic moiety is a ketone.

In an embodiment, the second polymerizable monomer is functionalized with an acetal moiety or a ketal moiety, as these moieties can be converted, after polymerization, to aldehyde or ketone moieties. In a further embodiment, the second polymerizable monomer is N-(2,2-dimethoxyethyl) methacryl amide, diacetone acrylamide, allylic aldehyde, 2-(methacryloyloxy)ethyl acetoacetate, and/or N-((2-methyl-1,3-dioxolan-2-yl)methyl)methacryl amide.

In other embodiments, the first and second precursor polymers are co-polymers which may further contain other monomers to adjust the properties of the final precursor polymers, and therefore, the hydrogel composition. In another embodiment, the first and second precursor polymers may also be modified after polymerization to introduce functional groups to the hydrogel composition.

In an embodiment, the hydrogel composition of the present disclosure comprises, a. the first precursor polymer which is a copolymer of sulfobetaine methacrylate and acrylic acid which is subsequently functionalized to contain hydrazide moeities;

b. the second precursor polymer which is a co-polymer of sulfobetaine methacrylate and N-(2,2-dimethoxyethyl) methacrylamide which is subsequently hydrolyzed to form aldehyde moieties and/or (N-((2-methyl-1,3-dioxolan-2-yl)methyl)methacrylamide), diacetone acrylamide, and/or 2-(methacryloyloxy)ethyl acetoacetate that has or can subsequently be hydrolyzed to have ketone moieties.

In an embodiment, the hydrogel compositions of the present disclosure comprise about 50 mol %, about 60 mol %, about 70 mol %, about 75 mol %, about 80 mol %, about 90 mol % or about 95 mol % of the zwitterionic monomer.

In another embodiment, the hydrogel compositions comprise a concentration of the hydrazide-functionalized zwitterionic polymer and a concentration of the aldehyde- and/or ketone-functionalized zwitterionic polymer in a range of about 10 mg/mL to about 600 mg/mL or about 20 mg/mL to about 300 mg/mL. In a further embodiment, the hydrogel compositions comprise a concentration of hydrazide-functionalized zwitterionic polymer and a concentration of aldehyde- and/or ketone-functionalized zwitterionic polymer in a range of about 50 mg/mL to about 200 mg/mL.

In an embodiment, the hydrogel compositions comprise a degree of functionalization comprising the hydrazide-functionalized zwitterionic polymer and the aldehyde- and/or ketone-functionalized zwitterionic polymer in the range of about 2 mol % to about 50 mol %. In another embodiment, the hydrogel compositions comprise a degree of functionalization comprising the hydrazide-functionalized zwitterionic polymer and the aldehyde- and/or ketone-functionalized zwitterionic polymer in the range of about 5 mol % to about 30 mol %

In an embodiment, the hydrogel compositions of the present application are chemically and mechanically tunable, for example, based on the selection and identity of the monomers of the precursor polymers. In one embodiment, the first and/or second precursor polymers include acrylic acid, methacrylic acid, itaconic acid, fumaric acid, maleic acid, vinylacetic acid or tert-butyl2-acryloylhydrazinecarboxylate, 2-dimethylaminoethylmethacrylate, 2-dimethylaminoethyacrylate, aminoethyl methacrylate, or allylamine to result in a pH-responsive hydrogel. In one embodiment, the hydrogels contain cell-specific ligands which results in a bioactive hydrogel. In another embodiment, two or more hydrazide-functionalized zwitterionic polymers and two or more aldehyde and/or ketone-functionalized zwitterionic polymers are mixed together to create hydrogels with intermediate properties to the constituent precursor polymers.

In one embodiment, any free radical polymerizable monomer such as vinylics, (meth)acrylics, (meth)acrylamides, allylics, or styrenics polymerizable with the zwitterionic monomer chosen can be used to functionalize the precursor polymers. In one embodiment, the co-monomer is a (meth) acrylic-type co-monomer.

In another embodiment of the disclosure, depending on the identity of the first and/or second precursor polymers, the hydrogel compositions have different gelation times. In one embodiment, immediate gelation is useful for drug delivery applications which avoid the drug from diffusing out of pre-gelled compositions. In other embodiments, gelation times of 2-90 minutes are favorable, for example, in biological barrier applications to enable the polymers to spread to fill gaps before gelation happens or to enable proper surgical or injection placement of the hydrogel. In other embodiments, gelation times of 30 minutes or greater are favorable, for example, in surface coating applications where large surface areas require equal distribution of the hydrogel.

In an embodiment, the mass-base swelling ratio relative to the dry state ($Q_m$), the rate of degradation, and the elastic storage modulus (G') of the hydrogel compositions of the present application are controlled by the degree of functionalization and the concentration of the hydrazide-functionalized zwitterionic polymer and the aldehyde- and/or ketone-functionalized zwitterionic polymer.

In an embodiment, the mass-based swelling ratio relative to the dry state ($Q_m$) is about 2.0 to about 100.0, about 3.0 to about 50.0, or about 4.0 to about 20.0. In a further embodiment, the elastic storage modulus (G') is about 0.05 kPa to about 100 kPa, about 0.1 kPa to about 50 kPa, or about 1.0 kPa to about 25 kPa.

In one embodiment, depending on the identity of the precursor polymers, the stability of the hydrogel compositions can be adjusted. In one embodiment, the hydrogel compositions of the present application are stable in vivo for period of at least about 3-12 months. In another embodiment, the hydrogel compositions of the present application are stable in vivo for period of at least 1 day, 2 days, 7 days, or 4 weeks.

In one embodiment, depending on the external environment, the hydrogel compositions of the present disclosure de-swell to a plateau water content of about 60% (w/w) water, about 70% (w/w) water, or about 80% (w/w) water. In another embodiment, the hydrogel compositions swell to about 90% (w/w) or about 99% (w/w) water.

In one embodiment, the hydrazone cross-linking, for example, by hydrazone bond formation, is useful in biomedical applications, as hydrazone bonds are degradable via hydrolysis as well as enzymatic action, and thus can break apart to release the lower molecular weight precursor polymers for clearance through the kidneys. In an embodiment, due to the reversible or degradable nature of the cross-linking bonds, the hydrogel compositions are degradable in vivo and reform the first and second precursor polymers having the same, or similar, molecular weight compared to the non-crosslinked precursor polymers. In one embodiment, the hydrogels have a molecular weight which is less than the molecular weight cut-off for renal (kidney) clearance. In another embodiment, the hydrogels have a molecular weight which is less than about 80 kDa, or less than about 60 kDa. In another embodiment, the hydrogels have a molecular weight of between about 10 to about 60 kDa, or about between about 20 to about 40 kDa.

In an embodiment, the hydrazide-functionalized zwitterionic polymer and the aldehyde- and/or ketone-functionalized zwitterionic polymer represent both the hydrogel precursor polymers as well as the hydrogel degradation products.

In an embodiment, the hydrogel compositions of the present application weakly binding to cells and proteins, and therefore minimize the inflammatory response when the hydrogels are used in biomedical applications (such as injection of a drug-loaded hydrogel). In another embodiment, the hydrogel compositions are non-cytotoxic. In an embodiment, the hydrogel compositions of the present application are injectable. In another embodiment, the hydrogel compositions of the present application are lubricious.

In one embodiment of the disclosure, the hydrogel compositions of the present disclosure are useful in biomedical applications including drug delivery vehicles, cell delivery vehicles, mechanical supports for soft tissue, biological lubricants, antifouling surfaces, and other applications. In another embodiment, the degradability (for example, acidic degradability) of the hydrogel compositions is useful as intracellular drug delivery vehicles (i.e. degradation would happen faster inside the endosome than outside the cell). In another embodiment, the swelling capacity of hydrogel composition can be used for superabsorbent applications such as diapers and other hygiene products.

In one embodiment of the disclosure, the hydrogel compositions are contained in a double-barreled syringe, comprising, a. a first barrel containing a first precursor polymer as defined in the present disclosure; and
b. a second barrel containing a second precursor polymer as defined in the present disclosure, wherein upon injection, the first and second precursor polymers form, in situ, the hydrogel composition as defined in the present disclosure.

In one embodiment, the double-barreled syringe further contains a drug and/or cells for the treatment of a condition. In one embodiment, the degradation time of the hydrogel can be altered by control the rate at which therapeutic or cells are released. In one embodiment, the in situ formed hydrogel composition is, for example, responsive to the environment in which it is located and can deliver a drug and/or cells based on environmental signals. In one such embodiment, the in situ formed hydrogel composition is pH responsive and degrades upon a decrease in pH, enabling the hydrogel composition to, for example, act as a drug delivery composition at a site of infection where the body is more acidic, under which conditions the hydrogel crosslinks dissociate faster and release the drug at a greater rate. In another embodiment, the hydrogel is used as a printable bioink to print hydrogel structures, with or without cells. In another embodiment, the hydrogel is used to 3D print cellularized tissue mimics useful for in vitro drug screening or in vivo biomedical implantation for cell therapy or tissue regeneration.

In one embodiment, the disclosure includes a method for encapsulating living cells, the method comprising a. providing a first and a second polymer;
b. mixing living cells with one of the first polymer or the second polymer;
c. co-printing or co-delivering the first and second polymers such that the polymers form a hydrogel composition with a defined geometry in situ which encapsulates the cells;

wherein the hydrogel composition, comprises the first polymer comprising monomeric units of i. one or more first polymerizable ethylenically unsaturated zwitterionic monomers containing at least one cationic charge and at least one anionic charge at neutral pH; and
ii. one or more polymerizable ethylenically unsaturated monomers functionalized with a nucleophilic moiety;

the second polymer comprising monomeric units of iii. one or more second polymerizable ethylenically unsaturated zwitterionic monomers containing at least one cationic charge and at least one anionic charge at neutral pH; and
iv. one or more polymerizable ethylenically unsaturated monomer functionalized with an electrophilic moiety, wherein the first and second polymers are crosslinked through covalent bonds by reaction of the nucleophilic and electrophilic moieties to form the hydrogel composition.

In another embodiment of the application, a pre-existing substrate can be coated with a hydrogel composition of the disclosure by:

a. adsorbing or reacting the first or second precursor polymer as defined herein on the substrate;
b. coating the substrate from step (i) with the complementary precursor polymer;
c. optionally repeating steps (i) and (ii), wherein the hydrogel composition is formed on the substrate. In one embodiment, the at least one first or at least one second precursor polymer are adsorbed, reacted, or coated on the substrate by dipping, printing, painting, spraying or delivering the polymers onto the substrate in any manner which results in the polymers forming the hydrogel compositions.

In one embodiment, the hydrogel compositions of the present disclosure are layered upon a substrate using a layer-by-layer dipping technique, wherein a precursor polymer is applied to the substrate to coat the substrate, such that at least some portion of the precursor polymer is adsorbed or reacted on the substrate. The first coat may either be the first precursor polymer or the second precursor polymer as described in the present disclosure. Upon coating with the first layer, the other (complementary) precursor polymer is subsequently coated on the substrate, wherein covalent cross-linking bonds (such as hydrazone bonds, when the precursor polymers are hydrazide and aldehyde- and/or ketone-functionalized) form between the two layers thereby forming a hydrogel on the substrate. This process is repeated as many times as desired using alternating precursor polymers to form a hydrogel coated substrate of different thickness. In another embodiment, the covalent cross-linking bonds, such as hydrazone bonds, formed on the substrate may subsequently be reduced to form non-degradable bonds. In one embodiment, the substrate is cellulose, polysulfone, poly(ether sulfone), cellulose acetate, or polyacrylonitrile. In another embodiment, the substrate is in the form of a membrane with a defined permeability. In other embodiments, substrates include biomaterials (in which suppressing protein adsorption suppresses inflammation), such as polyethylene, polyesters, silicones, or polymethyl methacrylate. In other embodiments, wastewater treatment membranes may be treated with hydrogel compositions which are low fouling.

In one embodiment, only a first precursor polymer is applied to the substrate to provide a functional polymer coating adsorbed, reacted or coated on the substrate by dipping, printing, painting, spraying or delivering the polymers onto the substrate in any manner which results in immobilization of the polymer on the surface.

In another embodiment, the hydrogel compositions of the present disclosure are applied in biosensing applications for minimizing non-specific, off-target binding to the biosensor. In a further embodiment, the biosensing applications include, but are not limited to, coatings to both solid and porous surfaces. In an embodiment, the coated solid and porous surfaces are prepared using a single or sequential layer-by-layer dipping technique analogous to polyelectrolyte layer-by-layer deposition using the hydrogel compositions of the present disclosure. In another embodiment, the solid and porous surfaces are coated for bioseparation applications. In a further embodiment, the solid and porous surfaces are coated to minimize non-specific protein adsorption. In one embodiment, the hydrogel compositions passivate the surface against non-specific binding and thereby increase the specificity and signal-to-noise of a sensing event.

In another embodiment, the hydrogel compositions of the present disclosure are applied for coating porous surfaces such as membranes or other porous media. In one embodiment, using the precursor polymer(s) of the present disclosure avoids the need to surface-functionalize materials prior to coating (wherein at least a portion of the precursor polymer is adsorbed or, with appropriate functional group chemistry, covalently bound on the substrate in a first application step) and enables the facile creation of thin-layer gel structure as opposed to brush structures (better suited to the delivery of bioactive agents from a protein passivation layer).

In one embodiment, the hydrogel compositions of the present disclosure are non-degradable hydrogel compositions. In an embodiment, the reversible hydrazone crosslink bonds are reduced by a suitable reducing agent to produce irreversible bonds. In another embodiment, the suitable reducing agents include, but are not limited to, sodium cyanoborohydride.

In one embodiment, the hydrogel compositions are useful in biological lubricant and/or viscosupplementation applications, wherein the hydrogel composition may be injected, implanted, or deposited. In an embodiment, the antifouling properties of the hydrogel prevent adsorption of fouling entities to the surface and thus suppress the inflammatory response to the material. In another embodiment, the hydrogel has coefficients of friction that are about 0.75 times to about 0.5 times to about 0.1 times that of commercially available biological lubricants. In another embodiment, the biological lubricants are applied to joint injections and cell delivery applications.

The first and/or second precursor polymers of the present application can be synthesized using any polymerization technique known in the art. In one embodiment, the precursor polymers are prepared using chain transfer free radical copolymerization. In another embodiment, the precursor polymers are prepared using controlled radical polymerization, including but not limited to atom transfer radical polymerization or reversible addition-fragmentation chain transfer polymerization, which allows for the preparation of such precursors having defined and narrow range of molecular weights, which in one embodiment aids in the ability of the hydrogels to be cleared from the body in, for example, drug delivery applications.

EXAMPLES

The following non-limiting examples are illustrative of the present applications of the hydrogel compositions of the present disclosure:

Materials:

N-(2,2-dimethoxyethyl)methacrylamide (DMEMAm) and N-((2-methyl-1,3-dioxolan-2-yl)methyl)methacrylamide (MDM) were synthesized according to reported protocols[19,33]. [2-(methacryloyloxy)ethyl] dimethyl-(3-sulfopropyl)ammonium hydroxide (DMAPS, Millipore Sigma, 95%), acrylic acid (AA, Millipore Sigma, 99%), ammonium persulfate (APS, Millipore Sigma), adipic acid dihydrazyde (ADH, Alfa Aesar, 98%), n'-ethyl-n-(3-dimethylaminopropyl)-carbodiimide (EDC, Carbosynth, commercial grade), 2-(methacryloyloxy)ethyl acetoacetate (AAEM, Millipore Sigma, 95%), diacetone acrylamide (DiAAAm, Millipore Sigma, 99%), hydrochloric acid (HCl, 100 mM, LabChem), bovine serum albumin (BSA, Millipore Sigma, >96%), fibrinogen from human plasma (Millipore Sigma, 50-70%), fluorescein isothiocyanate (FITC, Millipore Sigma), phalloidin-iFluor 488 reagent (Abcam) 4',6-diamidino-2-phenylindole (DAPI, ThermoFisher Scientific), and carboxyfluorescein diacetate succinimidyl ester kit (CellTrace CFSE, ThermoFisher) were all used as received. 3T3 mouse fibroblasts (ATCC: Cedarlane), C2C12 mouse myoblasts (ATCC: Cedarlane) were obtained from commercial suppliers. Media contents including Dulbecco's Modified Eagle Medium-high glucose (DMEM), fetal bovine serum (FBS), penicillin streptomycin (PS), and trypsin-EDTA and were purchased from Invitrogen Canada (Burlington, ON). For all experiments, Milli-Q grade water was used.

Example 1: Synthesis of Pre-polymers and Preparation of Hydrogels

Synthesis of Hydrazide-Functionalized Precursor (ZH):

ZH precursors were prepared by adding APS (40 mg, 0.175 mmol), DMAPS (4.0 g, 14.4 mmol), and AA (0.25 g, 3.5 mmol, for $ZH_{20}$) to a 250 mL Schlenk flask. 20 mL DIW was added and the solution was purged with nitrogen for at least 30 minutes. Subsequently, the flask was sealed and submerged in a pre-heated oil bath at 75° C. overnight under magnetic stirring. The resulting poly(DMAPS-co-AA) polymer was purified by dialysis against DIW for a minimum of 6 (6+ hour) cycles and lyophilized to dryness. The carboxylic acid groups of ZH precursor were subsequently converted to hydrazide groups via a carbodiimide-mediated conjugation of a large excess of adipic acid dihydrazide (ADH). The polymer (3.8 g) was dissolved in 100 mL DIW and added to a 250 mL round-bottom flask. ADH (3.1 g, 17.7 mmol, 5 mol eq.) was added and the pH of the solution adjusted to pH=4.75 using 0.1 M HCl. Subsequently, EDC (1.39 g, 8.9 mmol, 2.5 mol eq.) was added and the pH maintained at pH=4.75 by the dropwise addition of 0.1 M HCl over 4 hours. The solution was left to stir overnight, dialyzed against DIW for a minimum of 6 (6+ hour) cycles, and lyophilized. The degree of functionalization was determined using conductometric base-into-acid titration. The polymers were stored as 20 w/w % solutions in PBS at 4° C.

Synthesis of Aldehyde-Functionalized Precursor (ZA):

ZA precursors were prepared by adding APS (40 mg, 0.175 mmol), DMAPS (4.0 g, 14.4 mmol), and DMEMAm (0.62 g, 3.6 mmol, for $ZA_{20}$) to a 250 mL Schlenk flask. 20 mL DIW was added and the solution was purged with nitrogen for at least 30 minutes. Subsequently, the flask was sealed and submerged in a pre-heated oil bath at 75° C. overnight under magnetic stirring. After polymerization, the solvent was removed and the poly(DMAPS-co-DMEMAm) polymer was purified by dialysis against DIW for a minimum of 6 (6+ hour) cycles and lyophilized to dryness. The acetal groups of poly(DMAPS-co-DMEMAm) were subsequently converted to aldehydes by dissolving 3.5 g of the copolymer prepared above in 75 mL DIW and 25 mL 1.0 M HCl in a 250 mL round-bottom flask. The solution was left to stir for 24 hours, dialyzed for a minimum of 6 (6+ hour) cycles and lyophilized to dryness. The polymer was stored as 20 w/w % solution in PBS at 4° C.

Synthesis of Ketone-Functionalized Precursor (ZK):

ZK precursors were prepared by adding APS (40 mg, 0.175 mmol), DMAPS (4.0 g, 14.4 mmol), and either AAEM, diacetone acrylamide, or N-((2-methyl-1,3-dioxolan-2-yl)methyl)methacrylamide (3.6 mmol for $ZK_{20}$ and scaled appropriately for other compositions) to a 250 mL Schlenk flask. 20 mL DIW was added and the solution was purged with nitrogen for at least 30 minutes. Subsequently, the flask was sealed and submerged in a pre-heated oil bath at 75° C. overnight under magnetic stirring. After polymerization, the solvent was removed and the ZK polymer was purified by dialysis against DIW for a minimum of 6 (6+ hour) cycles and lyophilized to dryness. The polymer was stored as a 20 w/w % solution in PBS at 4° C.

Synthesis of Ketone-co-Aldehyde-Functionalized Precursor (ZK-co-A):

ZK-co-A precursors were prepared by adding APS (40 mg, 0.175 mmol), DMAPS (4.0 g, 14.4 mmol), DMEMAm (0.158 g, 0.91 mmol), and DiAAAm (0.462 g, 2.73 mmol, for $ZK_{15}$-co-$A_5$) to a 250 mL Schlenk flask. 20 mL DIW was added and the solution was purged with nitrogen for at least 30 minutes. Subsequently, the flask was sealed and submerged in a pre-heated oil bath at 75° C. overnight under magnetic stirring. After polymerization, the solvent was removed and the poly(DMAPS-co-DMEMAm-co-DiAAAm) polymer was purified by dialysis against DIW for a minimum of 6 (6+ hour) cycles and lyophilized to dryness. The polymer was stored as 20 w/w % solution in PBS at 4° C.

Chemical Characterization:

Aqueous size exclusion chromatography (SEC) was performed on a system consisting of a Waters 515 HPLC pump, Waters 717 plus autosampler, three Ultrahydrogel columns (30 cm×7.8 mm i.d.; exclusion limits: 0-3 kDa, 0-50 kDa, 2-300 kDa) and a Waters 2414 refractive index detector. A mobile phase consisting of 0.3 M sodium nitrate and 0.05 M phosphate buffer (pH 7) at a flow rate of 0.8 mL/min was used for all polymers analyzed, and the system was calibrated with narrow-dispersed poly(ethylene glycol) standards ranging from 106 to $584\times10^3$ g/mol (Waters). $^1$H-NMR was performed on a Bruker AVANCE 600 MHz spectrometer using deuterated chloroform as the solvent. The acrylic acid content of the polymers was determined using base-into-acid conductometric titration (ManTech Associates) using 50 mg of polymer dissolved in 50 mL of 1 mM NaCl as the analysis sample and 0.1 M NaOH as the titrant.

Figure 1:
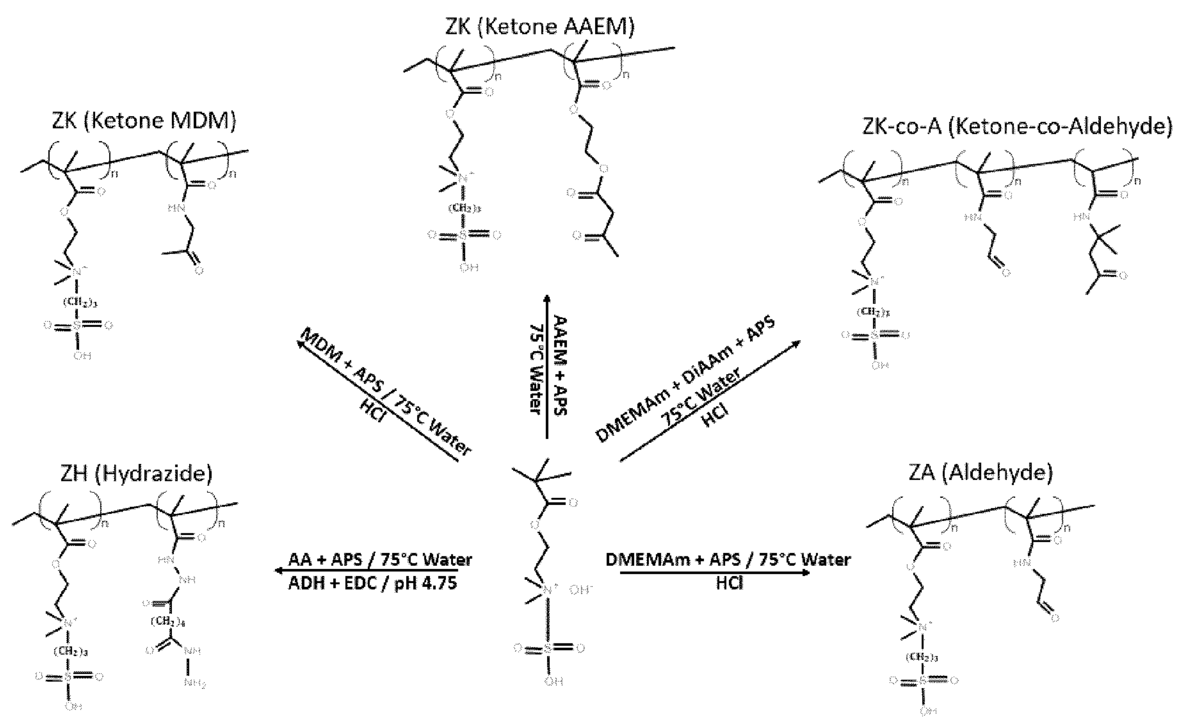

Results and Discussion:

Hydrazide-functionalized polyDMAPS precursors (ZH) were synthesized by conventional free radical polymerization of DMAPS and AA followed by post-polymerization conjugation of ADH using carbodiimide-catalyzed coupling. Aldehyde-functionalized polyDMAPS precursors (ZA) were synthesized by free radical polymerization of DMAPS and DMEMAm followed by acid-catalyzed deprotection of the acetal to form an aldehyde. Ketone-functionalized polyDMAPS precursors (ZK) were synthesized by free radical polymerization of DMAPS and one of the three ketone-containing or ketone precursor monomers described (AAEM, DiAAAm, or N-((2-methyl-1,3-dioxolan-2-yl)methyl)methacryl amide). Ketone-co-aldehyde-functionalized polyDMAPS precursors (ZK-co-A) were synthesized by free radical polymerization of DMAPS, DMEMAm, and DiAAAm followed by acid-catalyzed deprotection of the acetal to form an aldehyde. The syntheses performed and the chemical structures of the resulting zwitterionic polymers are depicted in FIG. 1. The number-average molecular weight of the precursor polymers was $40\text{-}60\times10^3$ g/mol. The molecular weight of the polymer precursors can be further controlled by modifying the duration of free radical polymerization or by adding additional chain transfer agent (e.g. TGA). The hydrazide, aldehyde, ketone, and ketone-co-aldehyde functionalized polymers are labelled according to their degrees of functionality y and z in the format $ZH_y$, $ZA_y$, $ZK_y$, and $ZK_y$-co-$A_z$, respectively, where y and z denote the mole percentage of each functional group relative to the total number of monomer residues in each precursor polymer.

Example 2: Physiochemical Properties of Hydrogels

Figure 2:
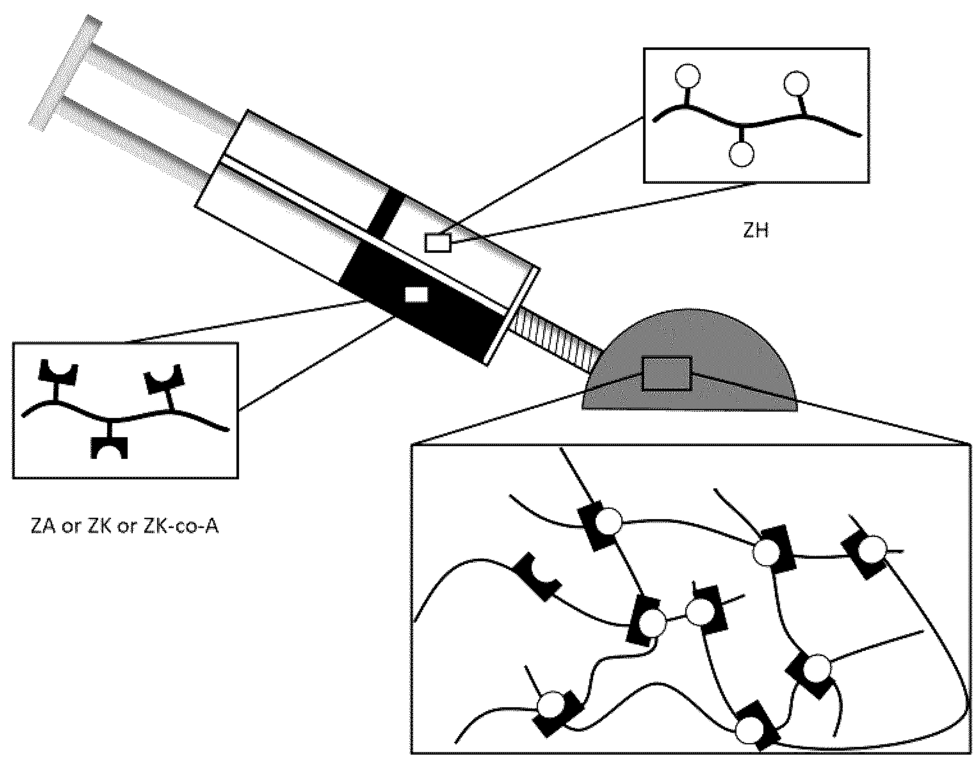

Preparation of Injectable Hydrogels:

Hydrogels were prepared via co-extrusion of hydrazide-functionalized (ZH) and aldehyde- and/or ketone-functionalized (ZA, ZK, or ZK-co-A) precursors dissolved in 10 mM PBS. Mechanical mixing of both polymer precursor solutions was achieved through the use of a double barrel syringe fitted with a static mixer at the outlet (Medmix Systems, L series). Hydrogel disks for all in vitro testing were prepared by extrusion of the reactive polymer precursors through the double barrel syringe into silicone molds of the shape and size relevant to the experiment followed by incubation at room temperature until the gels achieve equilibrium crosslinking prior to testing (FIG. 2).

Swelling Kinetics:

The swelling ratio of the hydrogels was determined by gravimetric measurements in 10 mM PBS at pH=7.4. Hydrogel pucks (n=3) with initial weight $W_0$ were placed into cell culture inserts that were placed in a 6-well cell culture plate and completely submerged with PBS. At predetermined time intervals, the cell culture inserts were removed from the well, the PBS was drained, and the hydrogels were gently dried to remove the non-absorbed PBS. The hydrogel disks were weighed ($W_t$) and completely re-submerged in fresh PBS solution and tested repeatedly for 1100 hours (45 days). Error bars represent the standard deviation of the replicate measurements. The swell ratio (SR) was determined dividing the mass at any time point ($W_t$) by the original mass ($W_0$).

Degradation Kinetics:

Degradation of the hydrogels was determined at 37° C. in 100 mM HCl at pH 1.0; these acid-catalyzed conditions were used to compare the degradation properties of the hydrogels on a more measurable time frame. Hydrogels (n=3) were placed into cell culture inserts that are subsequently placed in a 6-well cell culture plate and completely submerged with the HCl solution. At predetermined time intervals, the cell culture inserts were removed from the well, the HCl solution drained, and the hydrogel gently dried to wick off non absorbed solution prior to weighing of the hydrogel. Subsequently, the hydrogels were completely re-submerged in fresh HCl solution until the hydrogel was completely degraded (i.e. no separate phase was observed between the hydrogel and the HCl bath solution). Error bars represent the standard deviation of the replicate measurements.

Hydrogel Rheology:

The rheological properties of the hydrogels were measured using a Discovery Series Hybrid Rheometer (DHR) II rheometer (TA Instruments) operating under parallel-plate geometry with a plate diameter of 8 mm and a plate spacing of 1 mm. Rheological properties were measured by first conducting a flow sweep with shear rates of 0.01-100/s to identify the viscosity versus shear rate profile of the formulations. A strain sweep from 0.1-100% strain at 1 Hz was conducted to identify the linear viscoelastic range of the hydrogels. A strain was selected from within the linear range and set as a constant to perform a frequency sweep from 1 to 100 rad/s to measure shear elastic (G') and loss (G") moduli. All measurements were conducted at 25° C. in triplicate, with error bars representing the standard deviation of the replicate measurements.

Compressive Modulus:

Compressive modulus of the hydrogels was determined by performing unconstrained compression testing on a Biomomentum Mach-1 Mechanical Testing System. Hydrogels were formed with a cylindrical geometry (diameter 12.7 mm, height 3.5 mm) in silicone molds (diameter: 1.27 cm, height: 0.65 cm) and allowed to fully crosslink. The samples were compressed to 20% of the initial sample height at a rate of 0.03 mm per second to determine the Young's modulus.

Hydrogel Tribology:

The tribological properties of the hydrogels were measured using an Anton Paar $TRB^3$ tribometer operating in linear mode. Hydrogel pucks (n=3) were deposited and gelled on a glass microscope slide, ensuring consistent height with a silicone ring mold (diameter: 1.27 cm, height: 0.65 cm). A non-porous 6 mm alumina ball was aligned to the top of the gel with no load. Subsequently, 5 N of normal force was applied, and the ball was dragged linearly 4 mm across the gel over 100 cycles at 1 Hz. The coefficients of friction of the microscope slide and the gels were recorded as $\mu_m$ and $\mu_s$, respectively. The relative lubricity of the hydrogels was calculated by dividing the reciprocal of the coefficient of friction of the gel by the reciprocal of the coefficient of friction of the microscope slide. All measurements were done in triplicate, with the error bars representing the standard deviation of the replicate measurements.

Results and Discussion:

Zwitterionic hydrogels were prepared by extruding 50, 100, or 150 mg/mL each of $ZH_{20}$ and $ZA_{20}$, $ZH_{10}$ and $ZA_{10}$, and $ZH_5$ and $ZA_5$ solutions in 10 mM PBS using a double-barrel syringe. Specific nomenclature of the gels follows the format $ZN_x/E_y$ (W %) wherein N represents the combination of nucleophilic moieties, x represents the degree of functionality of the nucleophilic moieties, E represents the combination of the electrophilic moieties, y represents the degree of functionality of the electrophilic moieties, and W represents the polymer concentration in solution. For example, $ZH_{10}/A_{10}$ (15%) is a polyDMAPS hydrogel consisting of $ZH_{10}$ and $ZA_{10}$ at 15 wt % polymer in solution. In another example, $ZH_{20}/K_{15}$-co-$A_5$ (5%) is a polyDMAPS hydrogel consisting of $ZH_{20}$ and $ZK_{15}$-co-$A_5$ at 5 wt % polymer in solution. Depending on the precursor concentration and the degree of functionality, gelation occurs over time frames ranging from a several hours (~8 hours) to a few seconds (as little as <1 second) as required for each specific application; near-instantaneous gelation can be achieved using higher polymer concentrations or higher functional monomer contents (Table 1). Of note, the zwitterionic nature of the precursor polymers unexpectedly accelerates gelation by up to one order of magnitude relative to our previous observations with neutral poly(oligoethylene glycol methacrylate) (POEGMA)-based polymers crosslinked with a similar chemistry with similar concentrations/degrees of functionalization, allowing gelation at much lower polymer concentrations and/or polymer functionalization and thus additional versatility for applications.

Figure 3:
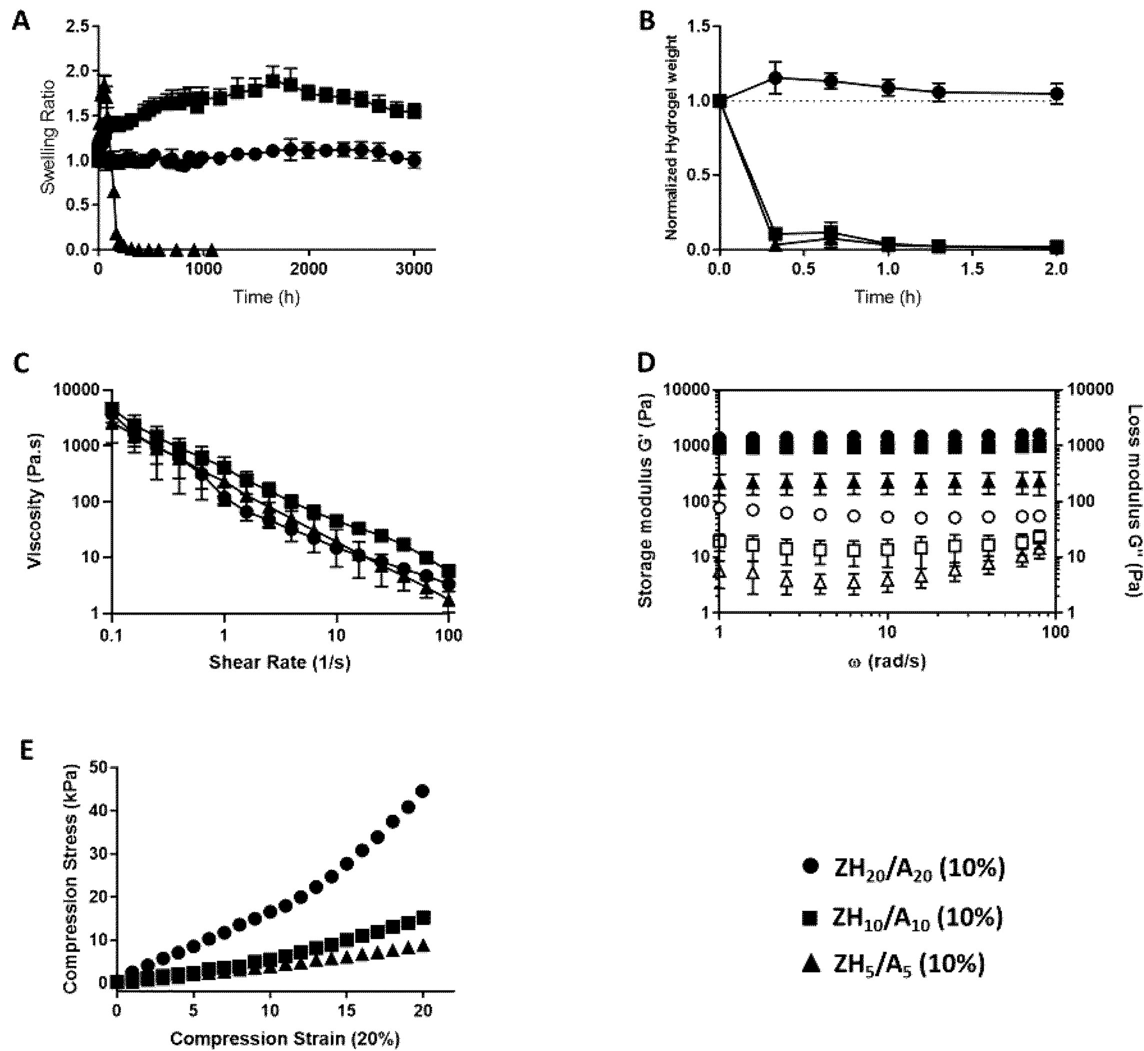

The hydrogels swell in PBS following preparation in PBS and reach equilibrium swelling after ~30 hours. The degree of functionalization of the hydrogels determines the crosslink density, which in turn controls the equilibrium mass-base swelling ratio (FIG. 3A), the rate of degradation (FIG. 3B), the viscosity (FIG. 3C), shear storage and loss moduli (FIG. 3D), and compressive modulus (FIG. 3E) of the resulting hydrogels. Of particular note, many formulations of polyDMAPS-based hydrogels are extremely stable and have slower degradation rates relative to neutral POEGMA-based polymers with similar crosslinking chemistry. Of additional note, $ZH_{20}/A_{20}$ (10%) and $ZH_{10}/A_{10}$ (10%) are both stable in PBS for longer than 4 months. Without wishing to be bound by theory, we attribute this enhanced stability of the gels to the synergistic effects between the covalent hydrazone crosslinking chemistry and the electrostatic interactions inherent with the zwitterionic nature of the monomers. Similarly, the combination of these crosslinking interactions enables enhanced mechanical properties (shear and compressive) of the hydrogels relative to previously reported injectable synthetic polymer-based hydrogels.

Figure 4:
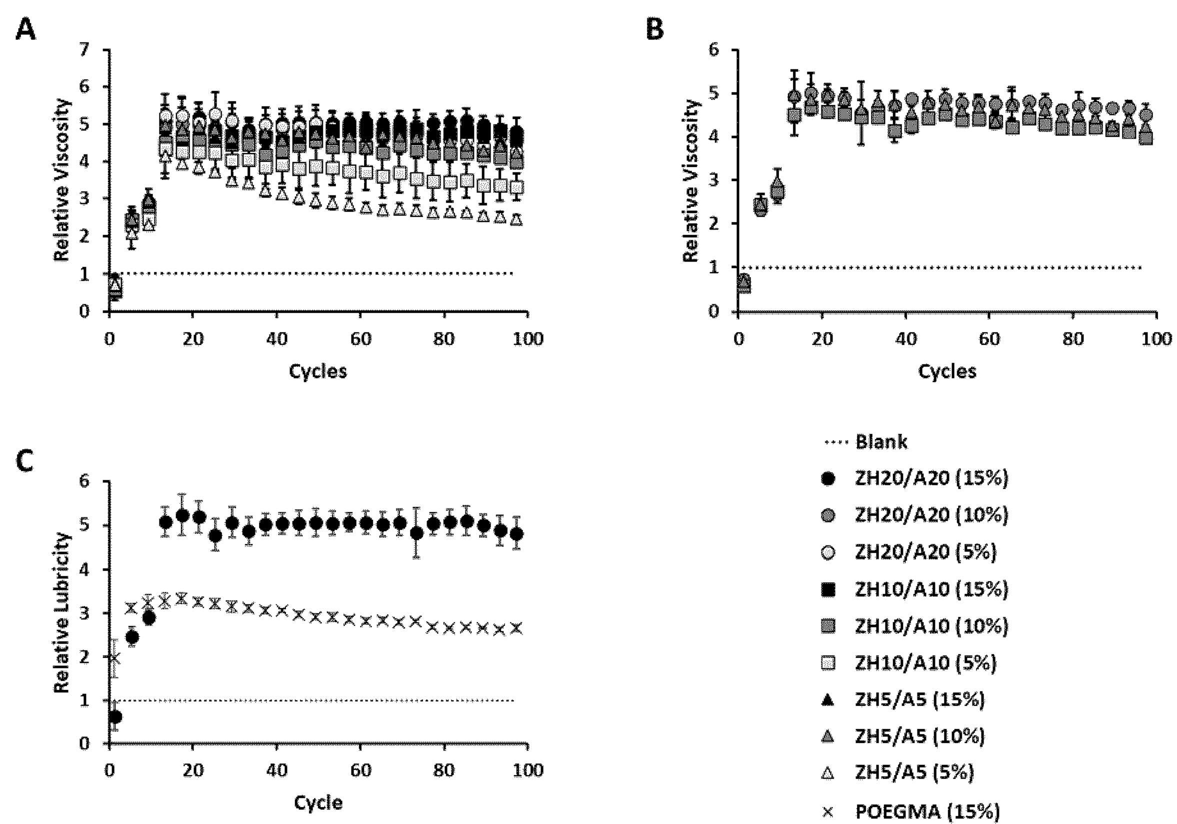

The tribological properties of the injectable zwitterionic hydrogels were evaluated to assess their lubricity by comparing different polyDMAPS formulations to similar POEGMA-based injectable gels crosslinked via hydrazone bonds. Ball-on-plate experiments with 5 N of normal load were performed. Most polyDMAPS injectable gels were shown to be about 5× more lubricating than a blank substrate, with no statistical difference between the different polyDMAPS hydrogels with exception to the very weak gel formulations $ZH_{10}/A_{10}$ (5%) and $ZH_5/A_5$ (5%) (FIG. 4A). PolyDMAPS hydrogels were also observed to be 60% more lubricious than the comparable POEGMA hydrogel (FIG. 4C). Furthermore, the lubricity of the zwitterionic gel formulations is largely unaffected by the degree of functionalization or the polymer concentration (FIG. 4B), allowing tuning of all other hydrogel properties (FIG. 3) without substantially reducing the highly favorable lubricity of the hydrogel.

Example 3: Biological Applications of Hydrogels

In Vitro Protein Adsorption Assay:

Protein absorption to the hydrogels was assayed in 96 well plates. ZH and ZA polymer solutions with 5%, 10%, or 20% degree of functionalization diluted in PBS (100 mg/mL) were sterilized, and 30 μL of each precursor solution was extruded into each well, mixed to ensure homogeneous gelation, and left overnight to ensure complete gelation. Once gelation was complete, 200 μL of 10 mM PBS was added to each well and hydrogels were allowed to swell to equilibrium prior to protein addition. Unabsorbed PBS was then removed, and 100 μL of either BSA-FITC or Fib-FITC solution (125, 250, 500, or 1000 μg/mL in PBS) was added. The hydrogels were incubated for 4 hours at 37° C. After 4 hours, the hydrogels were rinsed to remove unabsorbed protein and the fluorescence signal was measured using a Tecan Infinite M200 Pro plate reader using an excitation wavelength of 495 nm and an emission wavelength of 520 nm, comparing the stock solution controls. The gels were further tested using confocal laser scanning microscopy (CLSM, Nikon) to directly image and compare the fluorescence intensity of the hydrogels and the protein solutions. All measurements were done in triplicate, with the error bars representing the standard deviation of the replicate measurements.

In Vitro Cell Adhesion Assay:

Cell adhesion to the hydrogels was assayed in 48-well plates using 3T3 fibroblasts as a model cell. Hydrogels were directly extruded into each well, with 100 μL of each sterilized polymer precursor solution (100 mg/mL in 10 mM PBS) added, mixed, and then left overnight to ensure complete gelation. 200 μL of PBS was then added to each well, and the gels were allowed to swell to equilibrium. Excess PBS was removed, and the 3T3 cells were seeded on the top of the hydrogel at the density of $1\times10^5$ cells/well in 500 μL media and incubated for 24 hours at 37° C. After incubation, the media was removed, and the hydrogels and control wells were washed with PBS to remove non-adhered cells. The cells were fixed with 1 ml of 4% paraformaldehyde (w/v in PBS) in each well for 30 minutes and then stained by phalloidin-iFluor 488 reagent for 40 minutes and 2-(4-amidinophenyl)-6-indolecarbamidine dihydrochloride (DAPI) for 10 min. The well plate was imaged by confocal laser scanning microscopy (CLSM, Nikon), and fluorescence intensities were assessed. The number of cells was counted using ImageJ. All measurements were done in triplicate, with the error bars representing the standard deviation of the replicate measurements.

Bacteria Surface Adhesion Test:

Luria-Bertani (LB) broth was prepared by mixing LB (25 g) in 1000 mL distilled water and then sterilizing the resulting solution. *E. coli* was transferred to a tube containing LB broth and incubated at 37° C. for 24 h. The *E. coli* suspension was diluted 1000 times (1000×), and 1 mL of the diluted solution was transferred into each well of a 24 well plate. Fully swollen zwitterionic hydrogels were placed in the wells until completely immersed in the *E. coli* suspension and incubated at 37° C. for 12 h with shaking. The bacteria suspension was removed, and the hydrogels were washed by sterile PBS to remove non-adsorbed or loosely bound bacteria. The hydrogels were immersed into 3 mL PBS with shaking for 1 h to remove all loosely bound bacteria on the hydrogels. After that, the solution was diluted 1000× and 10 μL were transferred to spread on agar plates. The agar plates were incubated at 37° C. for 24 h, after which *E. coli* colony forming units were counted. All measurements were done in triplicate, with the error bars representing the standard deviation of the replicate measurements.

In Vitro Cellular Release from Hydrogel:

Cell release from the hydrogels was studied using C2C12 mouse myoblasts. Cells were labelled using carboxyfluorescein diacetate succinimidyl ester (CFSE) as per the kit instructions. Labeled cells were dispersed in media and then mixed into the ZH precursor such that the combined cell density of the cells in media and precursor polymer solution was $10^5$ cells/mL. 100 μL each of ZA (no cells) and ZH (loaded with cells) were dispensed into a 96-well plate and allowed to gel. Following, the gels were transferred from a 96-well plate to a 48-well plate and submerged in excess media (500 μL). The well plate was imaged at intervals of 24 hr, 72 hr, and 7 days by confocal laser scanning microscopy (CLSM, Nikon). Bright field imaging and fluorescence imaging (CFSE detection) were overlaid to identify the gel and cells, respectively.

In Vivo Host Response:

Host response of hydrogels was studied against BALB/C mice. ZH, and ZA precursors were prepared by dissolving the polymers in sterile PBS and further filtering them through a 0.3 μm syringe filter. Precursor polymers were loaded into sterile double barrel syringes and a total volume of 0.30 mL of precursor solution was injected subcutaneously in the scruff of the neck of 3-6 week old male BALB/C mice (Charles River) with a 22 G needle. After predetermined periods (2 days for acute, and 4 weeks for chronic) the mice were sacrificed and the gels and tissue surrounding the gel were excised and fixed in formalin for 24 hours. The fixed samples were trimmed and transferred to histology cassettes and stored in ethanol for at least 24 hours. Each tissue sample was then prepared for histology through wax fixation and haematoxylin and eosin (H&E). A grading system of host in vivo cytotoxicity of 0-4 was used, with each sample was attributed a score by a blinded observer. All experiments were performed in triplicate, with error bars representing the standard deviation of the replicate scores.

Figure 5:
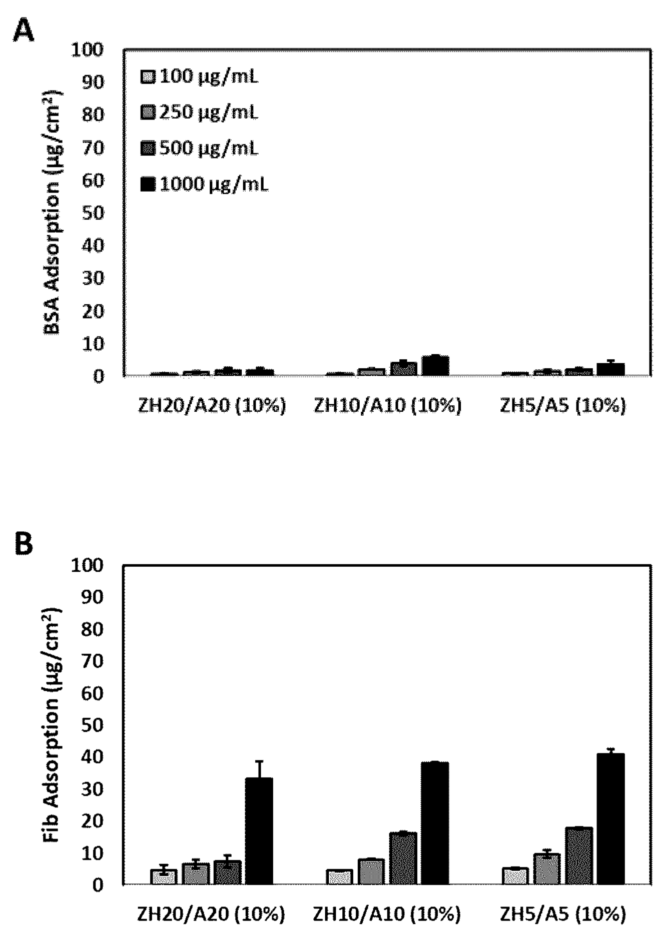
FIG. 5 shows, in one embodiment, the protein adsorption of bovine serum albumin (BSA) and fibrinogen (Fib) to a hydrogel of the disclosure as a function of the precursor polymer degree of functionality and the protein concentration of BSA (A) and Fib (B), respectively.
Figure 6:
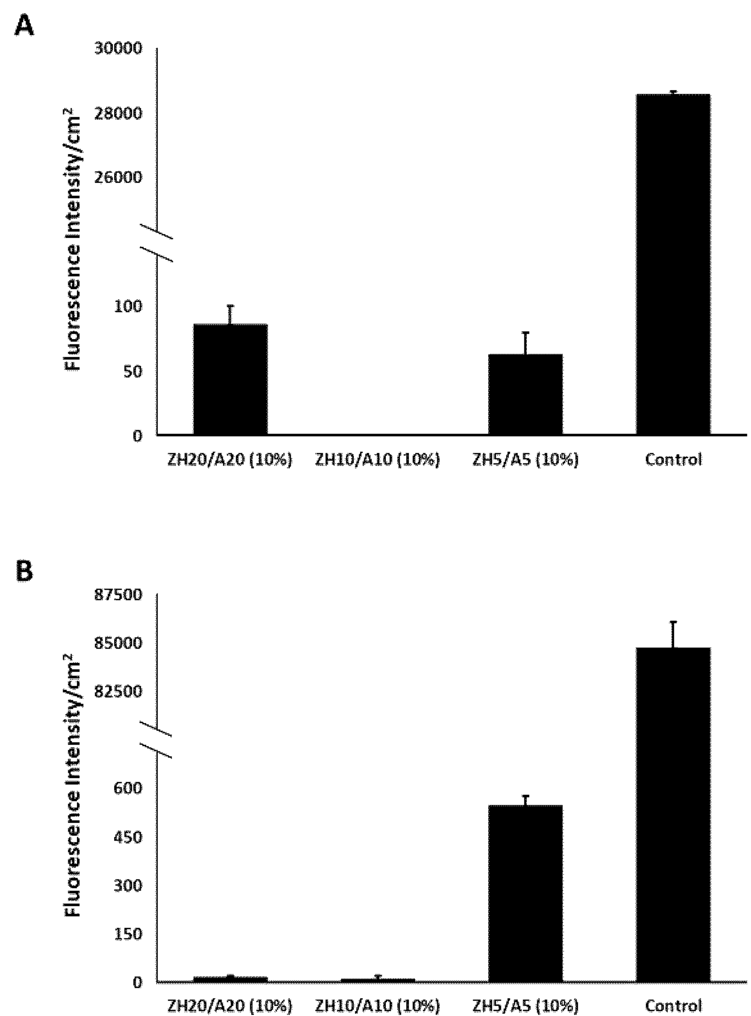
FIG. 6 shows, in one embodiment, the cellular adhesion of labeled 3T3 mouse fibroblasts. Fluorescent cell density as a function of precursor degree of functionality after 24 hours (A) and 72 hours (B), respectively.

Results and Discussion:

The bio-interfacial properties of the injectable zwitterionic hydrogels were evaluated using protein adsorption (FIG. 5) and cell adhesion (FIG. 6) assays. PolyDMAPS-based hydrogels (100 mg/mL for each of 5 mol %, 10 mol %, and 20 mol % reactive hydrazide and aldehyde group precursor polymers) were incubated with two abundant human plasma proteins, bovine serum albumin (BSA) and fibrinogen (Fib). The hydrogels exhibit excellent antifouling properties, adsorbing only about 3% and about 6.7% of BSA and fibrinogen, respectively (FIG. 5A, B), which is comparable or better than other sulfobetaine-based materials[34-36] as well as poly(ethylene glycol)-based interfaces commonly used as the gold-standard for biomaterials applications[3, 37, 38]

Figure 7:
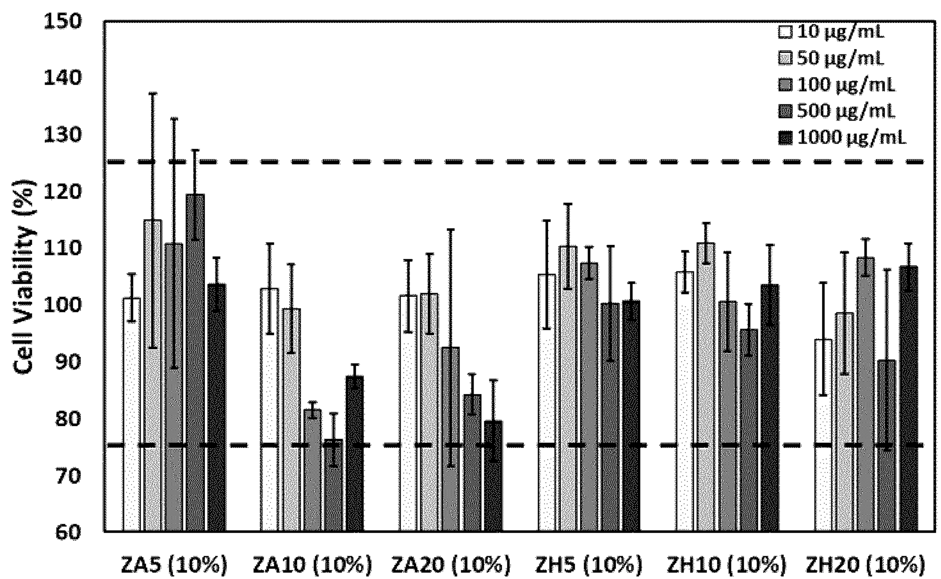
FIG. 7 shows the cell viability of 3T3 mouse fibroblasts and C2C12 mouse myoblasts after 24 h of exposure to precursor polymers of the disclosure in an embodiment of the disclosure. A) 3T3 mouse fibroblasts, B) C2C12 mouse myoblasts.
Figure 7:
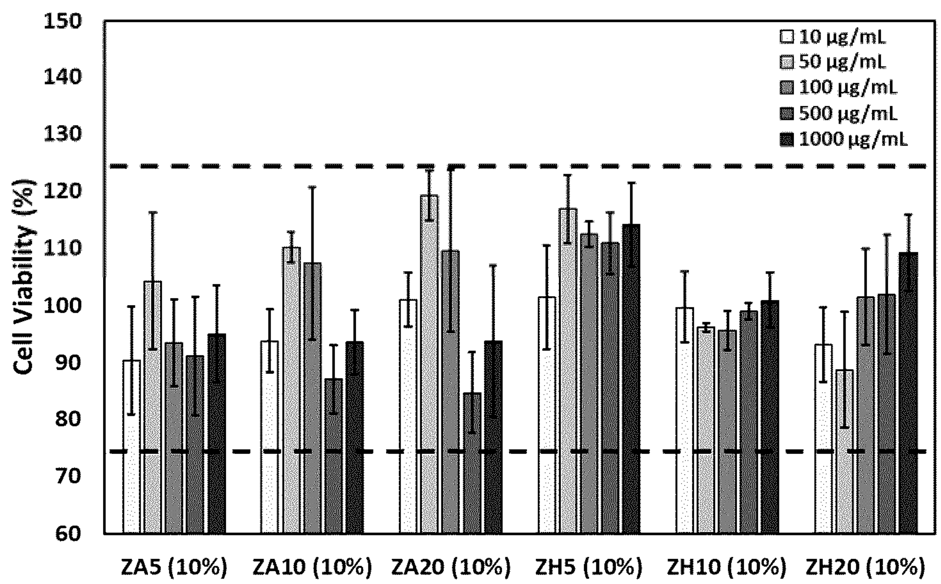

Cell adhesion of 3T3 mouse fibroblasts ($1\times10^5$ cells/well) to polyDMAPS zwitterionic hydrogels (prepared using 100 mg/mL solutions of 5 mol %, 10 mol %, and 20 mol % reactive hydrazide and aldehyde group precursor polymers) is minimal after 24 hr and 72 hr of incubation in relation to well plate controls. A ~400-fold decrease in cell adhesion (2.6 log) was noted after 24 hrs (FIG. 6A, C), while a 5600-fold reduction (3.7 log) in adhesion was noted for the 10 mol % and 20 mol % polyDMAPS-based hydrogels after 72 hours (FIG. 6B, D); the 5 mol % polyDMAPS-based gels exhibit a slightly lower 155-fold reduction (2.2 log) in cell adhesion after 72 hrs, with the somewhat lower anti-fouling properties attributed to gel degradation leading to more available space for cell proliferation and growth. The $ZH_y$ and $ZA_y$ polymers (representing both the individual precursor polymers and the formed hydrogels) did not impart any significant in vitro toxicity to 3T3 mouse fibroblasts or C2C12 mouse myoblasts after 24 hours of exposure even at concentrations far in excess of that of the degradation products (1000 μg/mL), suggesting that the degradation products of the material are cytocompatible (FIG. 7).

The bacterial adhesion of *E. coli* to the polyDMAPS-based gels was assessed by placing hydrogels (100 mg/mL solutions for each of 5 mol %, 10 mol %, and 20 mol % reactive hydrazide and aldehyde group precursor polymers) in diluted solutions of *E. coli* and incubating for 12 hours. Following, the hydrogels were gently washed with PBS to remove non-bound or loosely bound bacteria and then immersed in 3 mL PBS and subjected to strong shaking for 1 h. The fully detached bacteria were then plated at various dilutions on agar. $ZH_{20}/A_{20}$ (10%), $ZH_{10}/A_{10}$ (10%), and $ZH_5/A_5$ (10%) reduced adhesion by 75 fold, 90 fold, and 33 fold, respectively (FIG. 8A). The lower anti-adhesive properties of the $ZH_5/A_5$ (10%) are attributed to the significantly weaker mechanics of the gel coupled with its faster degradation over time.

The cell release of viable C2C12 mouse myoblasts as the hydrogels degrade was assessed against different polyDMAPS-based zwitterionic gel formulations. C2C12 cells were fluorescently labeled with Cell Trace CFSE as per kit instructions, and polyDMAPS-based gels were prepared using precursor polymers with 5 mol %, 10 mol %, and 20 mol % functional groups (all at a concentration of 10 wt %) were prepared with a cell density of $5\times10^3$ cells/gel in a 96 well-plate by adding the cells to the hydrazide component and incubating the gel over 4 hrs. The gels were then transferred to a 48 well-plate and submerged in excess media. Gels were imaged under confocal microscopy at intervals of 24 hrs, 72 hrs, 1 wk, and 2 wk. Cell release was noted to be directly related to gel degradation (FIG. 9, FIG. 3B), whereby the fastest degrading gel ($ZH_5/A_5$ (10%)) released the cells into the media while the slowest degrading gels kept the majority of the cells entrapped. However, high cell viability was maintained over the full 2 week period for cells remaining inside the hydrogels in all tested formulations; furthermore, cells released from the hydrogels could adhere and proliferate on the plate, confirming their high viability.

In vivo subcutaneous studies were carried out in BALB/C mice to assess the host response to the hydrogels. Mice were injected with different formulations of polyDMAPS-based gels and maintained and monitored for acute (2 day) and chronic (4 week) periods. During the monitoring period, mice did not exhibit any noticeable signs of discomfort per the grimace scale. Upon sacrifice, the hydrogels and surrounding tissue were excised from the subcutaneous space. PolyDMAPS-based gels had a significantly lower degree of adhesion and integration in the membrane when compared to injected POEGMA gels with similar physical properties and could be freely moved around the subcutaneous space, an atypical result for an injectable hydrogel.

Example 4: Surface Coating Applications of Hydrogels

Cellulose-based Surface Coating:

The use of polyDMAPS-based hydrogels for surface coating of membranes was assessed using a dip coating technique to modify cellulose acetate (CA) and nitrocellulose (NC) membranes. PolyDMAPS precursor polymers with 5%, 10%, or 20% mol degree of functionalization of aldehyde or hydrazide groups were dissolved in PBS at 40 mg/mL or 15 mg/mL. CA and NC membranes were completely submerged in ZA polymer solutions for 4 h at room temperature. The samples were removed from the solution, washed twice with PBS, and dried overnight at ambient conditions (~23° C. and ~30% relative humidity). Subsequently, the dried cellulose membranes were submerged in the complementary ZH solution for 4 hours, washed twice with PBS, and dried overnight. The process of dipping the membranes in ZA followed by ZH is considered one coating step, with subsequent sequential dipping of ZA and then ZH accordingly identified as the second, third, fourth, etc. coatings.

Surface Morphology:

Membranes were imaged by scanning electron microscopy (SEM) before and after surface coating with polyDMPAS. The samples were sputter-coated with gold (layer thickness=36 nm) to avoid charging effects and were imaged at a voltage of 20 kV using a working distance of 5 mm.

Water Contact Angle:

The effects of the hydrogel surface coating on the water contact angle of the membranes were assessed using a Model 100-00-115 NRL contact angle goniometer (Ramé-Hart, Succasunna, NJ) equipped with a Sanyo VC8-3512T camera. Contact angles were measured by applying 5 μL droplets of distilled deionized water on the surface of modified and unmodified CA and NC membranes. Droplets were tracked by video to track the initial contact angle as well as the kinetics of the penetration of the droplet through the membrane.

Protein Adsorption:

The effect of the hydrogel surface coatings on protein adsorption was assessed by submerging 0.5 cm×0.5 cm square membrane samples in PBS within wells of a 48 well plate and allowing the samples to hydrate over 24 hours. Unabsorbed PBS was then removed, and 1 mL of 100 μg/mL FITC-labeled protein solution (BSA or Fib) was added to each well. The samples were incubated for 4 hours at 25° C. under gentle shaking. After 4 hours, the membranes were removed and the residual protein concentration in the solution was measured against a standard curve using an Infinite M200 Pro (Tecan) plate reader.

Cell Adhesion:

To determine the cell adhesion on the dip-coated cellulose membranes, samples were cut into 0.5 cm×0.5 cm squares and submerged in PBS over 24 h to hydrate the membranes. Excess PBS was removed, and the 3T3 mouse fibroblast cells were seeded on the samples at the density of $1\times10^5$ cells/well suspended in 1000 μL of DMEM media. The cells were incubated for 24 h at 37° C., after which the media was removed and the samples were washed 3× with PBS to remove non-adhered cells. The cells were fixed by adding 1 mL of 4 w/v % paraformaldehyde in PBS in each well, incubating for 30 min, and staining the cells using phalloidin-iFluor 488 reagent (40 min.) and 2-(4-amidinophenyl)-6-indolecarbamidine dihydrochloride (DAPI, 10 min.) Cell adhesion was then assessed using confocal laser scanning microscopy (CLSM).

Results and Discussion:

The topographies of the native and polyDMAPS-based hydrogel-coated cellulose-based membranes were observed under SEM (FIG. 11). There is no significant morphological change to the membranes after one coating of the $ZH_5/A_5$ (4%) and $ZH_{10}/A_{10}$ (4%) hydrogels, which suggests these formulations are effective candidates for membrane surface coating. However, the morphology significantly changes after one coating of the fast-gelling hydrogel $ZH_{20}/A_{20}$ (4%), after which the membrane becomes completely smooth and the pores are blocked.

Water contact angle measurements on the CA and NC membranes before and after hydrogel coating (FIG. 12) showed that the coated membranes exhibited no significant change in the initial contact angle. Native and modified NC membranes both reached a terminal 0° contact angle within 5 s, suggesting rapid transport of water through the pores of the membrane even in the presence of the hydrogel coating (FIG. 12A). Water transport through the lower molecular weight cut-off CA membranes is much slower (~1740 s), with transport times increasing slightly upon hydrogel coating as a function of the degree of functionality of the applied polymers (~1810 s with one coating of $ZH_{10}/A_{10}$ (4%), ~2100 s with one coating of $ZH_{20}/A_{20}$ (4%)). However, overall, the hydrogel coating has a minimal impact on the water contact angle or water transport through the membrane.

The impact of polyDMAPS-based hydrogel coating on non-specific protein and cell adhesion was assessed using bovine serum albumin (BSA), fibrinogen (Fib), and 3T3 mouse fibroblasts (FIGS. 13-14). All surface-coating formulations used (5%, 10%, or 20% mol degree of functionality, dissolved at 40 mg/mL or 150 mg/mL polymer concentrations in PBS) demonstrated a reduction in protein adhesion, with the fibrinogen adsorption to the $ZH_{20}/A_{20}$ (15%) coating on the CA membrane reducing non-specific protein by two orders of magnitude; even the least notable change ($ZH_{10}/A_{10}$ (4%) on NC) offered a 66% reduction in BSA binding. Similar trends are observed with 3T3 mouse fibroblasts, with all hydrogels reducing cell adhesion by at least 90% and the $ZH_{20}/A_{20}$ hydrogels reducing cell adhesion by two full orders of magnitude. As such, despite the minimal changes observed in membrane transport properties, substantial decreases in fouling are achieved with the zwitterionic hydrogel coatings.

Example 5: Biological Lubricants and Viscosupplements

Polymer Synthesis

Hydrazide-functionalized zwitterionic precursor polymer (ZH) was synthesized by free-radical polymerization. 4 g of DMAPS and 0.176 g of AA ($ZH_{20}$) or 0.4422 g of AA ($ZH_{30}$) were added as monomers into a 250 mL single-neck round bottom flask. 40 mg of APS was added as the initiator, and all contents were dissolved in 20 mL DIW. The flask was purged in nitrogen for at least 30 minutes and subsequently submerged into a 75° C. oil bath to stir for 24 hr under $N_2$. The resulting polymer was subject to exhaustive dialysis against DIW (6 cycles, at least 6 hours/cycle), and lyophilized to get bulk polymer. The carboxylic acid groups of the AA were then converted to hydrazide groups via a carbodiimide-mediated conjugation of a large excess of adipic acid dihydrazide. The polymer was dissolved in DIW and transferred to a 250 ml round bottom flask. ADH (3.10 g for $ZH_{20}$ and 4.65 g for $ZH_{30}$) was added and allowed to dissolve, followed by the addition of EDC (1.40 g for $ZH_{20}$ and 2.08 g for $ZH_{30}$) The reaction was maintained at pH 4.75 using HCl over 4 hours and left to stir overnight at room temperature. The resulting solution was dialyzed against DIW as before and lyophilized to acquire the final ZH polymer. The polymer was dissolved in sterile PBS (20 w/w %) and passed through a 0.45 μm filter and stored in sterile conditions until needed. The degree of functionalization was calculated by ManTech automatic titrator base-into-acid titration. $^1H$ NMR spectrum was recorded on a Bruker AVANCE 600 MHz spectrometer, using deuterium oxide ($D_2O$) as the solvent.

Aldehyde-functionalized zwitterionic precursor polymer (ZA) was synthesized by free-radical polymerization. 4 g of DMAPS and 0.62 g of DMEMAm were added as monomers into a 250 mL single-neck round bottom flask. 40 mg of APS was added as the initiator, and all contents were dissolved in 20 mL DIW. The flask was purged in nitrogen for at least 30 minutes and subsequently submerged into a 75° C. oil bath to stir for 24 hr under $N_2$. The resulting polymer was deacetylated to expose aldehyde groups by the addition of 1 M HCl and overnight stirring. The material was then dialyzed against DIW (6 cycles, at least 6 hours/cycle) and lyophilized to get bulk polymer. The polymer was dissolved in sterile PBS (20 w/w %), passed through a 0.45 μm filter and stored in sterile conditions until needed. The degree of functionalization was analyzed by $^1H$ NMR spectrum in $D_2O$ on a Bruker AVANCE 600 MHz spectrometer.

Ketone-functionalized zwitterionic precursor polymer (ZK) was synthesized by free-radical polymerization. For AAEM-based polymers tested, 4 g of DMAPS, 0.686 g of AAEM, and 40 mg of APS were loaded into a 250 ml single-neck round bottom flask and dissolved in 20 mL of DIW. The flask was purged with $N_2$ for at least 30 minutes and subsequently submerged into a 75° C. oil bath and stirred for 24 hr under $N_2$. The resultant product was dialyzed against DIW for at least 6 cycles of 6 hours, lyophilized, and dissolved in sterile PBS (20 w/w %). The solution was then filtered through a 0.45 μm filter and stored in a refrigerator at 4° C. For the $ZK_{30}$ polymer made with N-((2-methyl-1,3-dioxolan-2-yl)methyl)methacrylamide (MDM) as the ketone comonomer, 4 g of DMAPS, 1.137 g of MDM, and 45 mg of APS was added, with the remainder of the procedure followed as above.

Ketone-co-aldehyde functionalized zwitterionic precursor polymer (ZK-co-A) was synthesized by co-polymerizing the zwitterionic monomer with both an aldehyde monomer and a ketone monomer (DiAAAm) using free-radical polymerization. 4 g of DMAPS, 0.462 g of DiAAAm, 0.158 g of DMEMAm, and 40 mg of APS were added to a 250 mL single-neck round bottom flask and dissolved in 20 mL of DIW. Following at least 30 minutes of $N_2$ purging, the flask was submerged in a 75° C. oil bath and stirred overnight under $N_2$. The aldehyde groups were formed by deacetylating the DMEMAm through the addition of HCl and stirring overnight. The polymer was dialyzed against DIW for at least 6 individual 6 hour cycles, lyophilized, dissolved in sterile PBS (20 w/w %), passed through a 0.45 μm filter, and stored at 4° C. until needed.

Hydrogel Preparation

Double barrel syringes with static mixers were loaded with the precursor polymers. Various formulations of ZH were loaded in one barrel, and the complimentary ZA or ZK or ZK-co-A were loaded in the other barrel. The contents were extruded through an attached static mixer and 25 G needle. Formulations that were not able to pass through the syringe were discarded, and the gelation time of the remaining formulations was assessed using an inversion test. Formulations with relevant gelation times (1 min-10 mins) were kept for further experimentation.

Viscoelastic Properties of Hydrogels

Rheology experiments were conducted on the zwitterionic hydrogel formulations in comparison to a leading market viscosupplement. Hydrogels were coextruded onto a Texas Instruments Discovery Hybrid Rheometer 2 (DHR2) loaded with a Peltier base set to 37° C. and a 20 mm parallel plate set at a height of 1000 μm. Following complete gelation of the gels on the plate (>30 minutes), a flow sweep was performed to analyze the viscosity shear response of the samples. The market hyaluronic acid-based viscosupplement, Orthovisc®, was subjected to the same experiments as a control.

Tribological Properties of Hydrogels

The coefficient of friction and the relative lubricity of the zwitterionic hydrogels were assessed on an Anton Paar TRB3 tribometer. Samples were extruded onto a non-porous alumina substrate within a 0.5 inch round silicone mold and allowed to fully gel. A silica ball with a 10 N load was placed onto the sample and subjected to a 4 mm linear motion at 0.5 Hz for 100 cycles followed by 100 cycles at a 5 Hz frequency. The same procedure was repeated to assess the lubricity of the market hyaluronic acid-based viscosupplement, Orthovisc® (control) and for a baseline measurement in which the silica ball is tested directly on the alumina sheet (simulating bone-on-bone contact). The coefficients of friction were recorded using the reciprocal analysis view to assess an average coefficient within each cycle under linear motion (disregarding the changing direction of the ball). The relative lubricity of the samples was quantified by dividing the measured hydrogel lubricity by the silica-alumina lubricity result.

Degradation Rates of Hydrogels In Vitro

The degradation rates of the various hydrogel formulations were studied by placing the gels in biologically relevant conditions. Sterile hydrogel formulations were coextruded (0.25 mL of each precursor polymer) and allowed to completely gel in a 0.5 inch round silicone mould. The hydrogels were then transferred into a 6 well-plate cell strainer and submerged in the wells of a 6 well-plate with CRL-1832 synoviocytes ($10^3$ cells/mL) in 5 mL of DMEM/F12 media. Media was replenished every 3 or 4 days, and cells were passaged weekly to the same concentration. At selected time-points (1 week, 2 weeks, 4 weeks, and 8 weeks), the gels were removed from the cell strainer, washed thoroughly with PBS, dried, and weighed. The mass of the dried hydrogels was normalized to the initial dried mass of hydrogels.

In Vivo Host Response of Hydrogels

Subcutaneous in vivo host responses of the hydrogels were studied using BALB/C mice. All protocols were approved by the Animal Research Ethics Board of McMaster University. Sterile double barrel syringes were loaded with the corresponding sterile precursor polymers in a biosafety cabinet. The hydrogels were injected into the subcutaneous space of the scruff behind the neck of the mice. The mice were allowed to roam freely in their cages and were monitored daily for signs of discomfort or sickness. After acute (2 days) and chronic (4 weeks) timepoints, the mice were sacrificed by $CO_2$ asphyxiation. The tissue surrounding the site of injection, as well as tissue to which gels were still attached were collected and analyzed by histology using an H&E stain.

Results and Discussion

Hydrogels were fabricated by co-extrusion through a double-barreled syringe. The gelation time is an important consideration for clinically relevant in situ gelling polymers; without wishing to be bound by theory, very short gelation times can be difficult to administer due to needle priming and the need for the surgeon to find the synovial space, while very long gelation times can be ineffective because of the potential for wash-out from the injection site and the impracticality of keeping patients still for extended periods. The gelation period was assessed using the vial inversion test, with the results of relevant zwitterionic hydrogel formulations reported in Table 2. Both hydrazide/aldehyde and hydrazide/ketone-co-aldehyde polymers can induce gelation within 1-10 minutes, the typically desired time for viscosupplement administration. Use of the less sterically hindered MDM ketone monomer as opposed to AAEM results in significantly faster gelation such that the ketone-only functionalized polymer $ZK_{30}$ can also induce gelation within the desired time window (Table 3).

Hydrogels with appropriate gelation times were then subjected to rheological analysis to assess their viscosity/shear thinning behavior. FIG. 15 shows that the viscosity of the hydrogels can match that of the native synovial fluid found in joints at appropriate polymer concentrations that still gel within the targeted 1-10 minute gelation time window. Furthermore, the hydrogels have similar viscosity properties to an existing leading commercial viscosupplement (Orthovisc®).

Tribology testing was carried out using an Anton Paar TRB3 tribometer by fabricating hydrogels in a 0.5 inch round silicone mold placed upon a non-porous sheet of alumina (to model bone) and then exposing the gels to 100 cycles of linear motion at 0.5 Hz (walking gait) and 100 cycles of linear motion at 5 Hz (running gait), with the coefficients of friction then measured and compared to the baseline of no hydrogel. FIG. 16 shows the relative lubricity of the hydrogels, which is inversely proportional to the coefficient of friction, normalized to the lubricity measured against the alumina sheet prepared with no hydrogel. Relative to a leading commercial formulation (Orthovisc®), the zwitterionic hydrogels exhibited 2-5-fold higher relative lubricities (i.e. 2-5-fold lower coefficients of friction) depending on the frequency range studied, suggesting their potential utility for joint lubrication.

The in vitro degradation of the hydrogels was then assessed using conditioned synoviocyte media, with the mass of the hydrogel measured as a function time to track both degradation and swelling over time. FIG. 17 shows that the injectable zwitterionic hydrogels can persist for significantly longer in the presence of synovial cell metabolites than the leading commercial viscosupplement (Orthovisc®), with one formulation able to exhibit minimal (<20%) swelling over the full one month observation period while the commercial material was almost entirely degraded within 3 days. Such stability accompanied by minimal swelling offers a beneficial combination of properties for long-term effective viscosupplementation.

Subcutaneous injection of the ZH20/A20 zwitterionic hydrogel (5 wt % polymers) was performed in mice, with a representative chronic (28 day) histological image from the injection shown in FIG. 18. The hydrogel appears to break apart into larger irregular particles rather than stay as a coherent mass, a feature that may further improve the weight bearing and shear thinning properties of the hydrogel in the joint; however, the material was largely retained after the one month period, consistent with the very slow synoviocyte conditioned media degradation rates observed. No significant inflammation was observed at the gel-tissue interface, nor was there any evidence of a fibrotic response. As such, the material appears to be well-tolerated in vivo.

TABLE 1

Gelation times for hydrogels prepared using precursor polymers with various concentrations and degrees of hydrazide/aldehyde functionalization.

| Hydrogel | Polymer concentration (wt %) | Gelation time (s) |
|---|---|---|
| $ZH_{20}/A_{20}$ | 15/15 | ~1 |
| $ZH_{20}/A_{20}$ | 10/10 | ~1 |
| $ZH_{20}/A_{20}$ | 5/5 | ~2 |
| $ZH_{10}/A_{10}$ | 15/15 | ~10 |
| $ZH_{10}/A_{10}$ | 10/10 | ~90 |
| $ZH_{10}/A_{10}$ | 5/5 | ~3600 |
| $ZH_5/A_5$ | 15/15 | ~210 |
| $ZH_5/A_5$ | 10/10 | ~3000 |
| $ZH_5/A_5$ | 5/5 | ~14,400 |

TABLE 2

Comparison of gelation times for zwitterionic hydrogels prepared by mixing a hydrazide-functionalized nucleophilic precursor polymer and aldehyde (DMAEAm) and/or ketone (DiAAAm)-functionalized electrophilic precursor polymers.

| Formulation | | | | |
|---|---|---|---|---|
| Precursor 1 | Precursor 1 Concentration (w/w %) | Precursor 2 | Precursor 2 Concentration (w/w %) | Gelation Time (s) |
| $ZH_2$ | 5 | $ZA_{20}$ | 5 | ~65 |
| $ZH_{10}$ | 10 | $ZA_{10}$ | 10 | ~90 |
| $ZH_5$ | 20 | $ZA_5$ | 20 | ~420 |
| $ZH_{20}$ | 10 | $ZK_{15}A_5$ | 10 | ~440 |
| $ZH_{20}$ | 7.5 | $ZK_{15}A_5$ | 7.5 | ~500 |

TABLE 3

Comparison of gelation times for zwitterionic hydrogels prepared by mixing a hydrazide-functionalized nucleophilic precursor polymer and MDM-functionalized electrophilic precursor polymers at different polymer concentrations

| Hydrogel | Polymer concentration (wt %) | Gelation time (s) |
|---|---|---|
| ZH30/K30 | 14/14 | ~480 |
| ZH30/K30 | 16/16 | ~325 |
| ZH30/K30 | 18/18 | ~190 |
| ZH30/K30 | 20/20 | ~150 |

REFERENCES

1. GhavamiNejad, A.; Park, C. H.; Kim, C. S., In situ synthesis of antimicrobial silver nanoparticles within antifouling zwitterionic hydrogels by catecholic redox chemistry for wound healing application. *Biomacromolecules* 2016, 17 (3), 1213-1223.
2. Song, J.; Zhu, Y.; Zhang, J.; Yang, J.; Du, Y.; Zheng, W.; Wen, C.; Zhang, Y.; Zhang, L., Encapsulation of AgNPs within Zwitterionic Hydrogels for Highly Efficient and Antifouling Catalysis in Biological Environments. *Langmuir* 2018, 35 (5), 1563-1570.
3. Harbers, G. M.; Emoto, K.; Greef, C.; Metzger, S. W.; Woodward, H. N.; Mascali, J. J.; Grainger, D. W.; Lochhead, M. J., Functionalized Poly(ethylene glycol)-Based Bioassay Surface Chemistry That Facilitates Bio-Immobilization and Inhibits Nonspecific Protein, Bacterial, and Mammalian Cell Adhesion. *Chemistry of Materials* 2007, 19 (18), 4405-4414.
4. Monteiro, D. R.; Gorup, L. F.; Takamiya, A. S.; Ruvollo-Filho, A. C.; de Camargo, E. R.; Barbosa, D. B., The growing importance of materials that prevent microbial adhesion: antimicrobial effect of medical devices containing silver. *International journal of antimicrobial agents* 2009, 34 (2), 103-110.
5. Zhang, L.; Cao, Z.; Bai, T.; Carr, L.; Ella-Menye, J.-R.; Irvin, C.; Ratner, B. D.; Jiang, S., Zwitterionic hydrogels implanted in mice resist the foreign-body reaction. *Nature Biotechnology* 2013, 31, 553.
6. Jansen, L. E.; Amer, L. D.; Chen, E. Y. T.; Nguyen, T. V.; Saleh, L. S.; Emrick, T.; Liu, W. F.; Bryant, S. J.; Peyton, S. R., Zwitterionic PEG-PC hydrogels modulate the foreign body response in a modulus-dependent manner. *Biomacromolecules* 2018, 19 (7), 2880-2888.
7. Geagea, R.; Aubert, P. H.; Banet, P.; Sanson, N., Signal enhancement of electrochemical biosensors via direct electrochemical oxidation of silver nanoparticle labels coated with zwitterionic polymers. *Chemical Communications* 2015, 51 (2),
8. Liu, N.; Xu, Z.; Morrin, A.; Luo, X., Low fouling strategies for electrochemical biosensors targeting disease biomarkers. *Analytical Methods* 2019, 11 (6), 702-711.
9. Zhao, W.; Zhu, Y.; Zhang, J.; Xu, T.; Li, Q.; Guo, H.; Zhang, J.; Lin, C.; Zhang, L., A comprehensive study and comparison of four types of zwitterionic hydrogels. *Journal of Materials Science* 2018, 53 (19), 13813-13825.
10. Laschewsky, A., Structures and Synthesis of Zwitterionic Polymers. *Polymers* 2014, 6 (5), 1544-1601.
11. Jiang, S.; Cao, Z., Ultralow-fouling, functionalizable, and hydrolyzable zwitterionic materials and their derivatives for biological applications. *Advanced materials* 2010, 22 (9), 920-932.
12. Bai, T.; Sun, F.; Zhang, L.; Sinclair, A.; Liu, S.; Ella-Menye, J. R.; Zheng, Y.; Jiang, S., Restraint of the differentiation of mesenchymal stem cells by a nonfouling zwitterionic hydrogel. *Angewandte Chemie International Edition* 2014, 53 (47), 12729-12734.
13. Yu, L.; Ding, J., Injectable hydrogels as unique biomedical materials. *Chemical Society Reviews* 2008, 37 (8), 1473-1481.
14. Smeets, N. M. B.; Bakaic, E.; Patenaude, M.; Hoare, T., Injectable poly (oligoethylene glycol methacrylate)-based hydrogels with tunable phase transition behaviours: Physicochemical and biological responses. *Acta biomaterialia* 2014, 10 (10), 4143-4155.
15. Chang, J.; Tao, Y.; Wang, B.; Guo, B.-h.; Xu, H.; Jiang, Y.-r.; Huang, Y., An in situ-forming zwitterionic hydrogel as vitreous substitute. *Journal of Materials Chemistry B* 2015, 3 (6), 1097-1105.
16. Li, Y.; Rodrigues, J.; Tomas, H., Injectable and biodegradable hydrogels: gelation, biodegradation and biomedical applications. *Chemical Society Reviews* 2012, 41 (6), 2193-2221.
17. Ren, Z.; Zhang, Y.; Li, Y.; Xu, B.; Liu, W., Hydrogen bonded and ionically crosslinked high strength hydrogels exhibiting Ca 2+-triggered shape memory properties and volume shrinkage for cell detachment. *Journal of Materials Chemistry B* 2015, 3 (30), 6347-6354.
18. Bakaic, E.; Smeets, N. M. B.; Badv, M.; Dodd, M.; Barrigar, O.; Siebers, E.; Lawlor, M.; Sheardown, H.; Hoare, T., Injectable and Degradable Poly (Oligoethylene glycol methacrylate) Hydrogels with Tunable Charge Densities as Adhesive Peptide-Free Cell Scaffolds. *ACS Biomaterials Science & Engineering* 2017, 4 (11), 3713-3725.

19. Smeets, N. M. B.; Bakaic, E.; Patenaude, M.; Hoare, T., Injectable and tunable poly (ethylene glycol) analogue hydrogels based on poly (oligoethylene glycol methacrylate). *Chemical Communications* 2014, 50 (25), 3306-3309.
20. Urosev, I.; Bakaic, E.; Alsop, R. J.; Rheinstädter, M. C.; Hoare, T., Tuning the properties of injectable poly (oligoethylene glycol methacrylate) hydrogels by controlling precursor polymer molecular weight. *Journal of Materials Chemistry B* 2016, 4 (40), 6541-6551.
21. Lutolf, M. P.; Lauer-Fields, J. L.; Schmoekel, H. G.; Metters, A. T.; Weber, F. E.; Fields, G. B.; Hubbell, J. A., Synthetic matrix metalloproteinase-sensitive hydrogels for the conduction of tissue regeneration: engineering cell-invasion characteristics. *Proceedings of the National Academy of Sciences* 2003, 100 (9), 5413-5418.
22. Obara, K.; Ishihara, M.; Ishizuka, T.; Fujita, M.; Ozeki, Y.; Maehara, T.; Saito, Y.; Yura, H.; Matsui, T.; Hattori, H., Photocrosslinkable chitosan hydrogel containing fibroblast growth factor-2 stimulates wound healing in healing-impaired db/db mice. *Biomaterials* 2003, 24 (20), 3437-3444.
23. Qiu, Y.; Park, K., Environment-sensitive hydrogels for drug delivery. *Advanced drug delivery reviews* 2001, 53 (3), 321-339.
24. Blackman, L. D.; Gunatillake, P. A.; Cass, P.; Locock, K. E. S., An introduction to zwitterionic polymer behavior and applications in solution and at surfaces. *Chem Soc Rev* 2019, 48 (3), 757-770.
25. Lee, C.-J.; Wu, H.; Hu, Y.; Young, M.; Wang, H.; Lynch, D.; Xu, F.; Cong, H.; Cheng, G., Ionic Conductivity of Polyelectrolyte Hydrogels. *ACS Applied Materials & Interfaces* 2018, 10 (6), 5845-5852.
26. De France, K. J.; Chan, K. J. W.; Cranston, E. D.; Hoare, T., Enhanced mechanical properties in cellulose nanocrystal-poly (oligoethylene glycol methacrylate) injectable nanocomposite hydrogels through control of physical and chemical cross-linking. *Biomacromolecules* 2016, 17 (2), 649-660.
27. Dong, D.; Li, J.; Cui, M.; Wang, J.; Zhou, Y.; Luo, L.; Wei, Y.; Ye, L.; Sun, H.; Yao, F., In Situ "Clickable" Zwitterionic Starch-Based Hydrogel for 3D Cell Encapsulation. *ACS Appl Mater Interfaces* 2016, 8 (7), 4442-55.
28. Sinclair, A.; O'Kelly, M. B.; Bai, T.; Hung, H. C.; Jain, P.; Jiang, S., Self-Healing Zwitterionic Microgels as a Versatile Platform for Malleable Cell Constructs and Injectable Therapies. *Adv Mater* 2018, 30 (39), e1803087.
29. Sundaram, H. S.; Han, X.; Nowinski, A. K.; Ella-Menye, J. R.; Wimbish, C.; Marek, P.; Senecal, K.; Jiang, S., One-step dip coating of zwitterionic sulfobetaine polymers on hydrophobic and hydrophilic surfaces. *ACS Appl Mater Interfaces* 2014, 6 (9), 6664-71.
30. Sundaram, H. S.; Han, X.; Nowinski, A. K.; Brault, N. D.; Li, Y.; Ella-Menye, J. R.; Amoaka, K. A.; Cook, K. E.; Marek, P.; Senecal, K.; Jiang, S., Achieving One-step Surface Coating of Highly Hydrophilic Poly(Carboxybetaine Methacrylate) Polymers on Hydrophobic and Hydrophilic Surfaces. *Adv Mater Interfaces* 2014, 1 (6).
31. He, H.; Xiao, Z.; Zhou, Y.; Chen, A.; Xuan, X.; Li, Y.; Guo, X.; Zheng, J.; Xiao, J.; Wu, J., Zwitterionic poly (sulfobetaine methacrylate) hydrogels with optimal mechanical properties for improving wound healing in vivo. *J Mater Chem B* 2019, 7 (10), 1697-1707.
32. Chen, Y.; Wang, W.; Wu, D.; Nagao, M.; Hall, D. G.; Thundat, T.; Narain, R., Injectable Self-Healing Zwitterionic Hydrogels Based on Dynamic Benzoxaborole-Sugar Interactions with Tunable Mechanical Properties. *Biomacromolecules* 2018, 19 (2), 596-605.
33. Patenaude, M.; Campbell, S.; Kinio, D.; Hoare, T., Tuning Gelation Time and Morphology of Injectable Hydrogels Using Ketone-Hydrazide Cross-Linking. *Biomacromolecules* 2014, 15 (3), 781-790.
34. Lee, S. Y.; Lee, Y.; Le Thi, P.; Oh, D. H.; Park, K. D., Sulfobetaine methacrylate hydrogel-coated anti-fouling surfaces for implantable biomedical devices. *Biomater Res* 2018, 22, 3.
35. Lu, A.; Wu, Z.; Luo, X.; Li, S., Protein adsorption and macrophage uptake of zwitterionic sulfobetaine containing micelles. *Colloids Surf B Biointerfaces* 2018, 167, 252-259.
36. Su, Y.-l.; Li, C., Controlled adsorption of bovine serum albumin on poly(acrylonitrile)-based zwitterionic membranes. *Reactive and Functional Polymers* 2008, 68 (1), 161-168.
37. Du, H.; Chandaroy, P.; Hui, S. W., Grafted poly-(ethylene glycol) on lipid surfaces inhibits protein adsorption and cell adhesion. *Biochim. Biophys. Acta-Biomembr.* 1997, 1326 (2), 236-248.
38. Xu, L. C.; Siedlecki, C. A., Protein adsorption, platelet adhesion, and bacterial adhesion to polyethylene-glycol-textured polyurethane biomaterial surfaces. *J. Biomed. Mater. Res. Part B* 2017, 105 (3), 668-678.

The invention claimed is:

1. A hydrogel composition, comprising a. at least one first polymer comprising monomeric units of
   i. one or more first polymerizable ethylenically unsaturated zwitterionic monomers containing at least one cationic charge and at least one anionic charge at neutral pH; and
   ii. one or more polymerizable ethylenically unsaturated monomers functionalized with a nucleophilic moiety;
b. at least one second polymer comprising monomeric units of
   i. one or more second polymerizable ethylenically unsaturated zwitterionic monomers containing at least one cationic charge and at least one anionic charge at neutral pH; and
   ii. one or more polymerizable ethylenically unsaturated monomer functionalized with an electrophilic moiety, wherein the electrophilic moiety of at least one polymerizable ethylenically unsaturated monomer comprises a ketone group; and wherein the first and second polymers are crosslinked through covalent bonds by reaction of the nucleophilic and electrophilic moieties to form the hydrogel composition.

2. The hydrogel composition of claim 1, wherein the first and second zwitterionic moieties independently or simultaneously have the structure

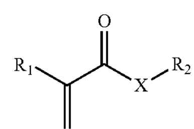

wherein

X is O or NR', wherein R' is H or $(C_1-C_6)$-alkyl;

$R_1$ is H, $(C_1-C_{10})$-alkyl, OH, or —O—$(CH_2)_x$ where x is an integer between 1 and 10;

$R_2$ is a hydrocarbyl moiety containing an anionic moiety and a cationic moiety.

3. The hydrogel composition of claim 2, wherein the first and second zwitterionic moieties independently or simultaneously have the structure

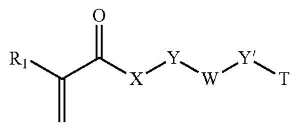

wherein

X is O or NR', wherein R' is H or $(C_1-C_6)$-alkyl;

$R_1$ is H, $(C_1-C_{10})$-alkyl, OH, or —O—$(CH_2)_x$ where x is an integer between 1 and 10;

Y and Y' are independently or simultaneously $(C_1-C_{10})$-alkylene, optionally wherein one or more carbon atoms are replaced with oxygen atoms;

W is a cationic moiety or an anionic moiety; and

T is an anionic moiety or a cationic moiety, wherein when W is a cationic moiety, T is an anionic moiety, and when W is an anionic moiety, T is a cationic moiety, and wherein the net charge of the monomer is zero.

4. The hydrogel composition of claim 3, wherein the cationic moiety is an amine or ammonium moiety.

5. The hydrogel composition of claim 4, wherein the amine moiety is —NR'— and the ammonium moiety is —$N^+$R'R"—, wherein R' and R" are independently or simultaneously H or $(C_1-C_6)$-alkyl.

6. The hydrogel composition of claim 3, wherein the anionic moiety is a sulfate, carboxyl, phosphate, or boronate moiety.

7. The hydrogel composition of claim 3, wherein the first and second zwitterionic monomers independently or simultaneously have the structure

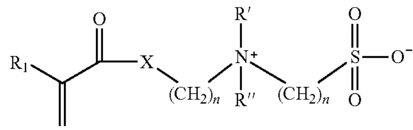

wherein,

X is O or NR', wherein R' is H or $(C_1-C_6)$-alkyl $R_1$ is H, $(C_1-C_{10})$-alkyl, OH, or —O—$(CH_2)_x$ where x is an integer between 1 and 10;

R' and R" are independently or simultaneously H or $(C_1-C_6)$-alkyl; and n is an integer from 1 to 10.

8. The hydrogel composition of claim 7, wherein the first and second zwitterionic monomers have the structure

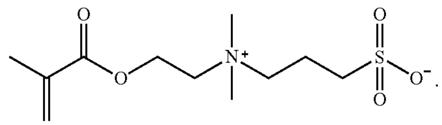 [SMILES: C=C(C)C(=O)OCC[N+](C)(C)CCCS(=O)(=O)[O-]]

9. The hydrogel composition of claim 1, wherein the polymerizable ethylenically unsaturated monomer functionalized with a nucleophilic moiety has the formula

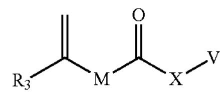

wherein

X is O or NR', wherein R' is H or $(C_1-C_6)$-alkyl;

$R_3$ is H or $(C_1-C_6)$-alkyl;

M is $(C_0-C_3)$-alkylene; and

V is a hydrocarbyl moiety containing a nucleophilic moiety.

10. The hydrogel composition of claim 9, wherein the polymerizable ethylenically unsaturated monomer functionalized with a nucleophilic moiety has the formula

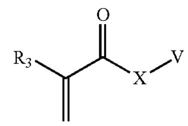

wherein

X is O or NR', wherein R' is H or $(C_1-C_6)$-alkyl;

$R_3$ is H or $(C_1-C_6)$-alkyl; and

V is a hydrocarbyl moiety containing a nucleophilic moiety.

11. The hydrogel composition of claim 9, wherein the polymerizable ethylenically unsaturated monomer functionalized with a nucleophilic moiety has the formula

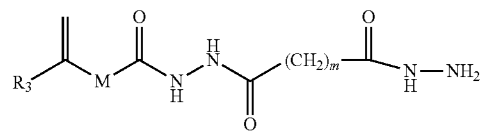

wherein m is 1-10 and $R_3$ is H or $(C_1-C_6)$-alkyl.

12. The hydrogel composition of claim 10, wherein the polymerizable ethylenically unsaturated monomer functionalized with a nucleophilic moiety has the formula

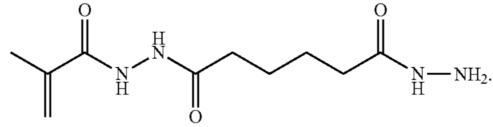 [SMILES: C=C(C)C(=O)NNC(=O)CCCCC(=O)NN]

13. The hydrogel composition of claim 1, wherein polymerizable ethylenically unsaturated monomer functionalized with an electrophilic moiety has the formula

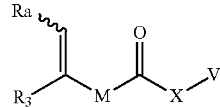

wherein

X is O or NR', wherein R' is H or $(C_1-C_6)$-alkyl;

Ra is H or —COOH;

$R_3$ is H or $(C_1-C_6)$-alkyl, wherein the $(C_1-C_6)$-alkyl group is optionally substituted with a —COOH group;

M is $(C_0-C_3)$-alkylene; and

V is a hydrocarbyl moiety containing at least one electrophilic moiety, wherein at least one electrophilic moiety comprises a ketone group.

14. The hydrogel composition of claim 13, wherein polymerizable ethylenically unsaturated monomer functionalized with an electrophilic moiety has the formula

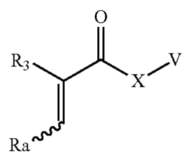

wherein

X is O or NR', wherein R' is H or $(C_1-C_6)$-alkyl;

Ra is H or —COOH;

$R_3$ is H or $(C_1-C_6)$-alkyl, wherein the $(C_1-C_6)$-alkyl group is optionally substituted with a —COOH group;

V is a hydrocarbyl moiety containing at least one electrophilic moiety.

15. The hydrogel composition of claim 13, wherein the polymerizable ethylenically unsaturated monomer functionalized with an electrophilic moiety has the formula

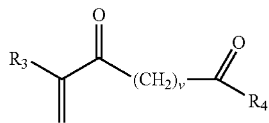

wherein $R_3$ is H or $(C_1-C_6)$-alkyl;

$R_4$ is H, $(C_1-C_{10})$-alkyl, wherein one or more $CH_2$ groups in $(C_1-C_{10})$-alkyl are optionally replaced with C═O;

v is an integer from between 1 and 10; and wherein one or more carbon atoms in the group $(CH_2)$ y are optionally replaced with oxygen atoms or nitrogen atoms (NH or NR' wherein R' is $C_1-C_6$-alkyl).

16. The hydrogel composition of claim 15, wherein the polymerizable ethylenically unsaturated monomer functionalized with an electrophilic moiety has the formula

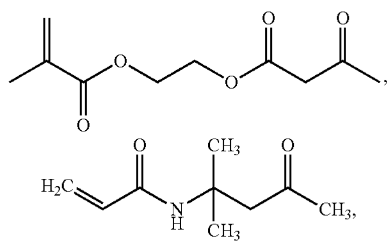

-continued

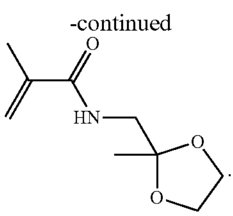

17. The hydrogel composition of claim 1, wherein the nucleophilic moiety is a hydrazide or amine derivative, a carbonyl hydrate, an alcohol, cyanohydrin or cyanohydrin derivative, a thiol or thiol derivative, or a phosphorus ylide or derivatives thereof.

18. The hydrogel composition of claim 1, wherein at least one electrophilic moiety comprises a ketone group, and the second polymer may further comprise monomers having an aldehyde, a ketone, a carboxylic acid, an ester, an amide, a maleimide, an acyl (acid) chloride, an acid anhydride or an alkene group or derivatives thereof.

19. The hydrogel composition of claim 1, wherein the first and second polymers are crosslinked through hydrazone bonds.

20. The hydrogel composition of claim 9, wherein the polymerizable ethylenically unsaturated monomer is derived from acrylic acid or a derivative thereof, methacrylic acid, itaconic acid, fumaric acid, maleic acid, or vinylacetic acid.

21. The hydrogel composition of claim 1, wherein the a polymerizable ethylenically unsaturated monomer functionalized with a nucleophilic moiety is N-(2,2-dimethoxyethyl) methacrylamide, (N-((2-methyl-1,3-dioxolan-2-yl) methyl) methacrylamide), diacetone acrylamide, allylic aldehyde, 2-(methacryloyloxy) ethyl acetoacetate, and/or N-((2-methyl-1,3-dioxolan-2-yl) methyl) methacrylamide.

22. A method for the lubrication and/or viscosupplementation of a joint comprising administering to the joint of a subject a hydrogel composition, comprising a. at least one first polymer comprising monomeric units of
   i. one or more first polymerizable ethylenically unsaturated zwitterionic monomers containing at least one cationic charge and at least one anionic charge at neutral pH; and
   ii. one or more polymerizable ethylenically unsaturated monomers functionalized with a nucleophilic moiety;
b. at least one second polymer comprising monomeric units of
   i. one or more second polymerizable ethylenically unsaturated zwitterionic monomers containing at least one cationic charge and at least one anionic charge at neutral pH; and
   ii. one or more polymerizable ethylenically unsaturated monomer functionalized with an electrophilic moiety, wherein the electrophilic moiety of at least one polymerizable ethylenically unsaturated monomer comprises a ketone group wherein the first and second polymers are crosslinked through covalent bonds by reaction of the nucleophilic and electrophilic moieties to form the hydrogel composition.

23. The method of claim 22, wherein the first and second polymers are intra-articularly injected into the joint of the subject and the hydrogel compositions forms in situ.

24. The method of claim 22, wherein the hydrogel further comprises a therapeutic agent.

* * * * *